United States Patent

Kanayama

(10) Patent No.: US 8,999,267 B2
(45) Date of Patent: Apr. 7, 2015

(54) AUTOMATIC ANALYZER

(75) Inventor: Shoichi Kanayama, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/075,524

(22) Filed: Mar. 30, 2011

(65) Prior Publication Data

US 2011/0243791 A1 Oct. 6, 2011

(30) Foreign Application Priority Data

Apr. 1, 2010 (JP) .................................. 2010-085239

(51) Int. Cl.
| | | |
|---|---|---|
| *B01L 3/02* | (2006.01) | |
| *G01N 35/10* | (2006.01) | |
| *G01N 35/02* | (2006.01) | |
| *G01N 35/04* | (2006.01) | |
| *G01N 35/00* | (2006.01) | |

(52) U.S. Cl.
CPC .......... *G01N 35/025* (2013.01); *B01L 2300/046* (2013.01); *B01L 2200/141* (2013.01); *G01N 2035/0405* (2013.01); *G01N 2035/00277* (2013.01); *G01N 35/10* (2013.01); *G01N 2035/00287* (2013.01)

(58) Field of Classification Search
CPC .......... G01N 2035/00277; G01N 2035/00287; G01N 2035/0405
See application file for complete search history.

(56) References Cited

U.S. PATENT DOCUMENTS

| | | | |
|---|---|---|---|
| 2003/0129094 A1* | 7/2003 | Schubert et al. | .............. 422/100 |
| 2009/0191095 A1 | 7/2009 | Nakamura | |

FOREIGN PATENT DOCUMENTS

| | | |
|---|---|---|
| CN | 1346058 A | 4/2002 |
| CN | 101038292 A | 9/2007 |
| CN | 101071138 A | 11/2007 |
| CN | 101135694 A | 3/2008 |
| CN | 101236194 A | 8/2008 |
| CN | 101419240 A | 4/2009 |
| CN | 101632025 A | 1/2010 |
| JP | 3-175362 | 7/1991 |
| JP | 6-102282 | 4/1994 |
| JP | 6-160398 | 6/1994 |

OTHER PUBLICATIONS

Chinese Office Action issued Aug. 21, 2013, in China Patent Application No. 201110082122.6 (with English translation).
Combined Office Action and Search Report issued Dec. 30, 2013 in Chinese Patent Application No. 201310196625.5 (with English language translation).
Japanese Office Action issued Oct. 7, 2014 in Japanese Patent Application No. 2011-070741 w/ English Translation.

* cited by examiner

*Primary Examiner* — P. Kathryn Wright
(74) *Attorney, Agent, or Firm* — Oblon, McClelland, Maier & Neustadt, L.L.P.

(57) ABSTRACT

According to one embodiment, an automatic analyzer includes a reaction disc, cleaning mechanism, and cover. The reaction disc holds a cuvette which contains a sample and a reagent. The cleaning mechanism is configured to clean the cuvette using a nozzle. The cover is configured to be movable along an axis of the nozzle and to cover an opening of the cuvette.

2 Claims, 19 Drawing Sheets

Standby mode

Cleaning operation skip (OFF) mode

|  | Cleaning position a | Cleaning position b | Cleaning position c | Cleaning position d | Cleaning position e | Cleaning position f | Cleaning position g | Cleaning position h |
|---|---|---|---|---|---|---|---|---|
| Cleaning pattern A | High-concentration waste liquid | Alkaline cleaner cleaning | Acidic cleaner cleaning | Water cleaning | Water cleaning | Water cleaning | Suction | Drying |
| Cleaning pattern B | High-concentration waste liquid | Alkaline cleaner cleaning | Alkaline cleaner cleaning | Water cleaning | Water cleaning | Water cleaning | Suction | Drying |
| Cleaning pattern C | High-concentration waste liquid | Acidic cleaner cleaning | Alkaline cleaner cleaning | Water cleaning | Water cleaning | Water cleaning | Suction | Drying |
| Cleaning pattern D | High-concentration waste liquid | Water cleaning | Water cleaning | Water cleaning | Water cleaning | Water cleaning | Suction | Drying |
| Cleaning pattern E | High-concentration waste liquid | Acidic cleaner cleaning | Acidic cleaner cleaning | Water cleaning | Water cleaning | Water cleaning | Suction | Drying |

F I G. 3

|  | Cleaning position a | Cleaning position b | Cleaning position c | Cleaning position d | Cleaning position e | Cleaning position f | Cleaning position g | Cleaning position h |
|---|---|---|---|---|---|---|---|---|
| Cuvette A | High-concentration waste liquid | Alkaline cleaner cleaning | Acidic cleaner cleaning | Water cleaning | Water cleaning | Water cleaning | Suction | Drying |
| Cuvette B | High-concentration waste liquid | Alkaline cleaner cleaning | Alkaline cleaner cleaning | Water cleaning | Water cleaning | Water cleaning | Suction | Drying |
| Cuvette C | High-concentration waste liquid | Acidic cleaner cleaning | Alkaline cleaner cleaning | Water cleaning | Water cleaning | Water cleaning | Suction | Drying |
| Cuvette D | High-concentration waste liquid | Alkaline cleaner cleaning | Water cleaning | Water cleaning | Water cleaning | Water cleaning | Suction | Drying |
| Cuvette E | High-concentration waste liquid | Acidic cleaner cleaning | Water cleaning | Water cleaning | Water cleaning | Water cleaning | Suction | Drying |
| Cuvette F | High-concentration waste liquid | Water cleaning | Water cleaning | Water cleaning | Water cleaning | Water cleaning | Suction | Drying |

F I G. 4

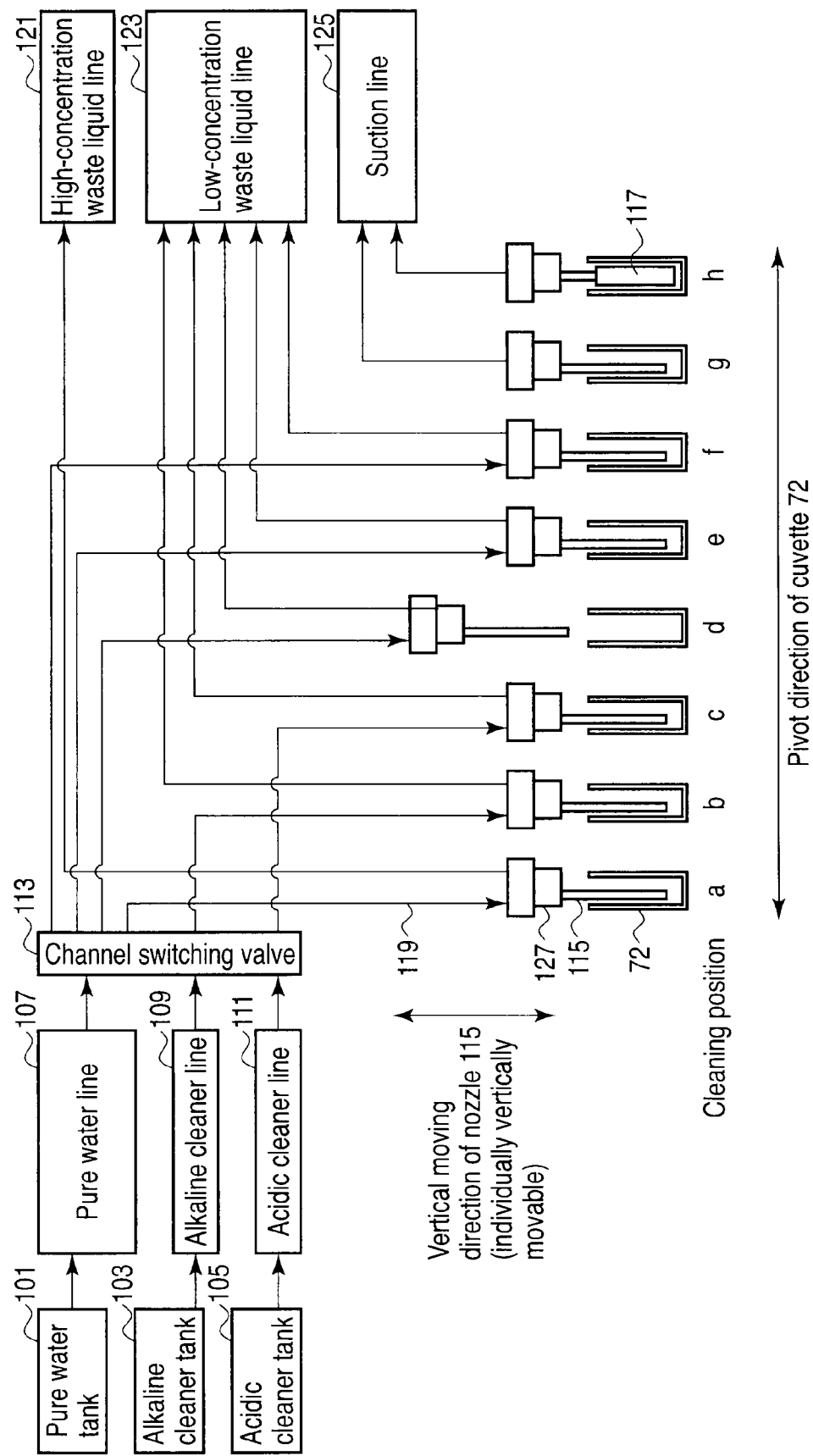
F I G. 5

| Cleaning position / Pivot cycle | Cleaning position a | Cleaning position a | Cleaning position a | Cleaning position a | Cleaning position a | Cleaning position a | Cleaning position a | Cleaning position a |
|---|---|---|---|---|---|---|---|---|
| C1 | Cuvette A | Cuvette B | Cuvette C | Cuvette D | Cuvette E | Cuvette F | Cuvette G | Cuvette H |
| C2 | ... | ... | ... | ... | ... | ... | ... | ... |
| ... | ... | ... | ... | ... | ... | ... | ... | ... |
| Cn+1 | Cuvette Z | Cuvette A | Cuvette B | Cuvette C | Cuvette D | Cuvette E | Cuvette F | Cuvette G |
| Cn+2 | ... | ... | ... | ... | ... | ... | ... | ... |
| ... | ... | ... | ... | ... | ... | ... | ... | ... |
| C2n+1 | Cuvette Y | Cuvette Z | Cuvette A | Cuvette B | Cuvette C | Cuvette D | Cuvette E | Cuvette F |
| C2n+2 | ... | ... | ... | ... | ... | ... | ... | ... |
| ... | ... | ... | ... | ... | ... | ... | ... | ... |
| Cm*n+1 | Cuvette A | Cuvette B | Cuvette C | Cuvette D | Cuvette E | Cuvette F | Cuvette G | Cuvette H |

F I G. 8

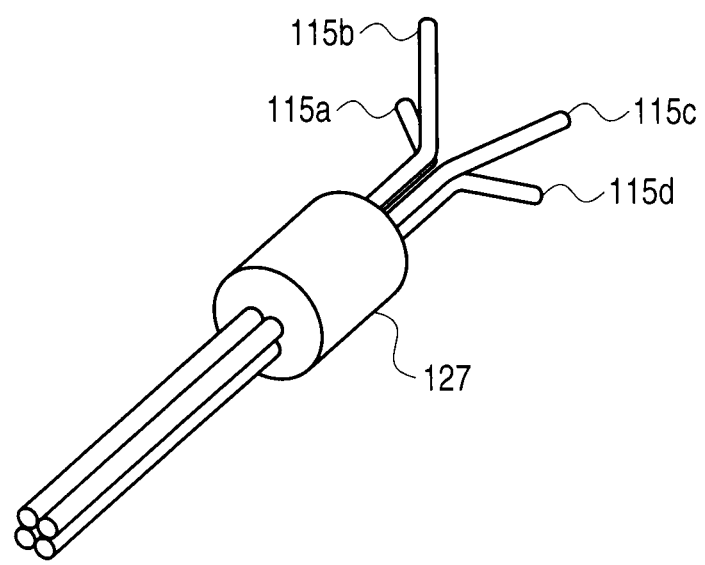
F I G. 1 0

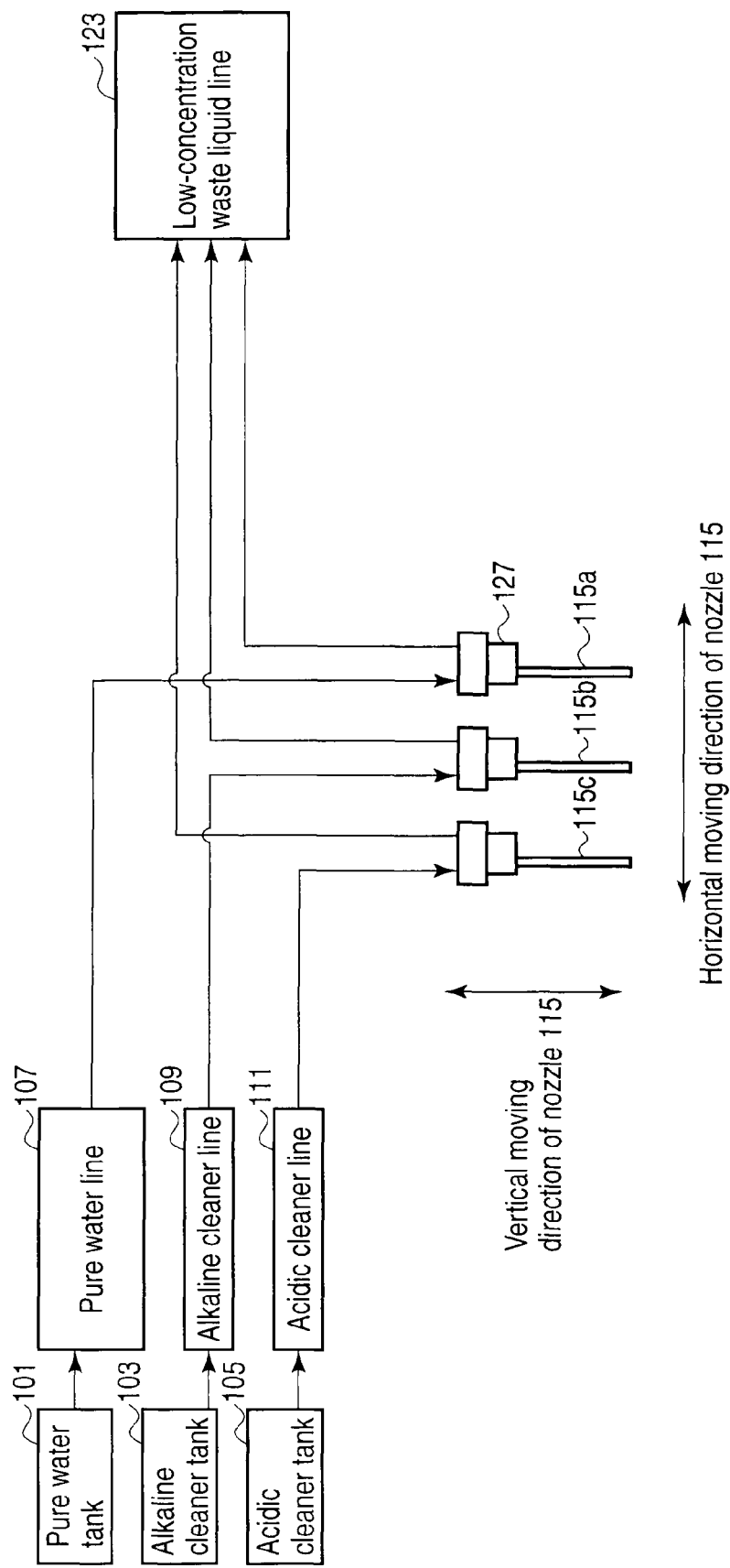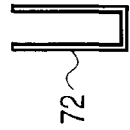
FIG. 12

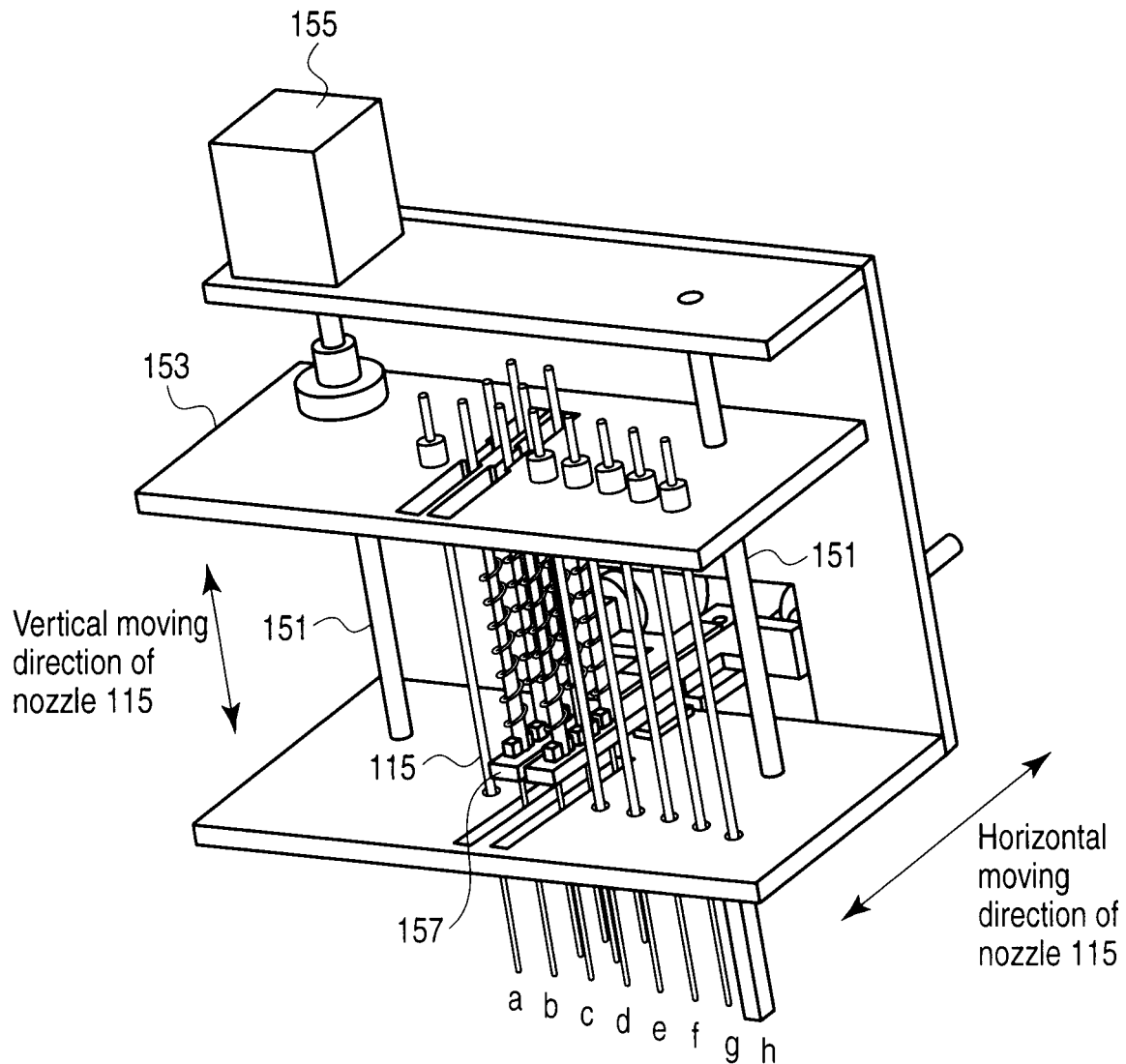
F I G. 13

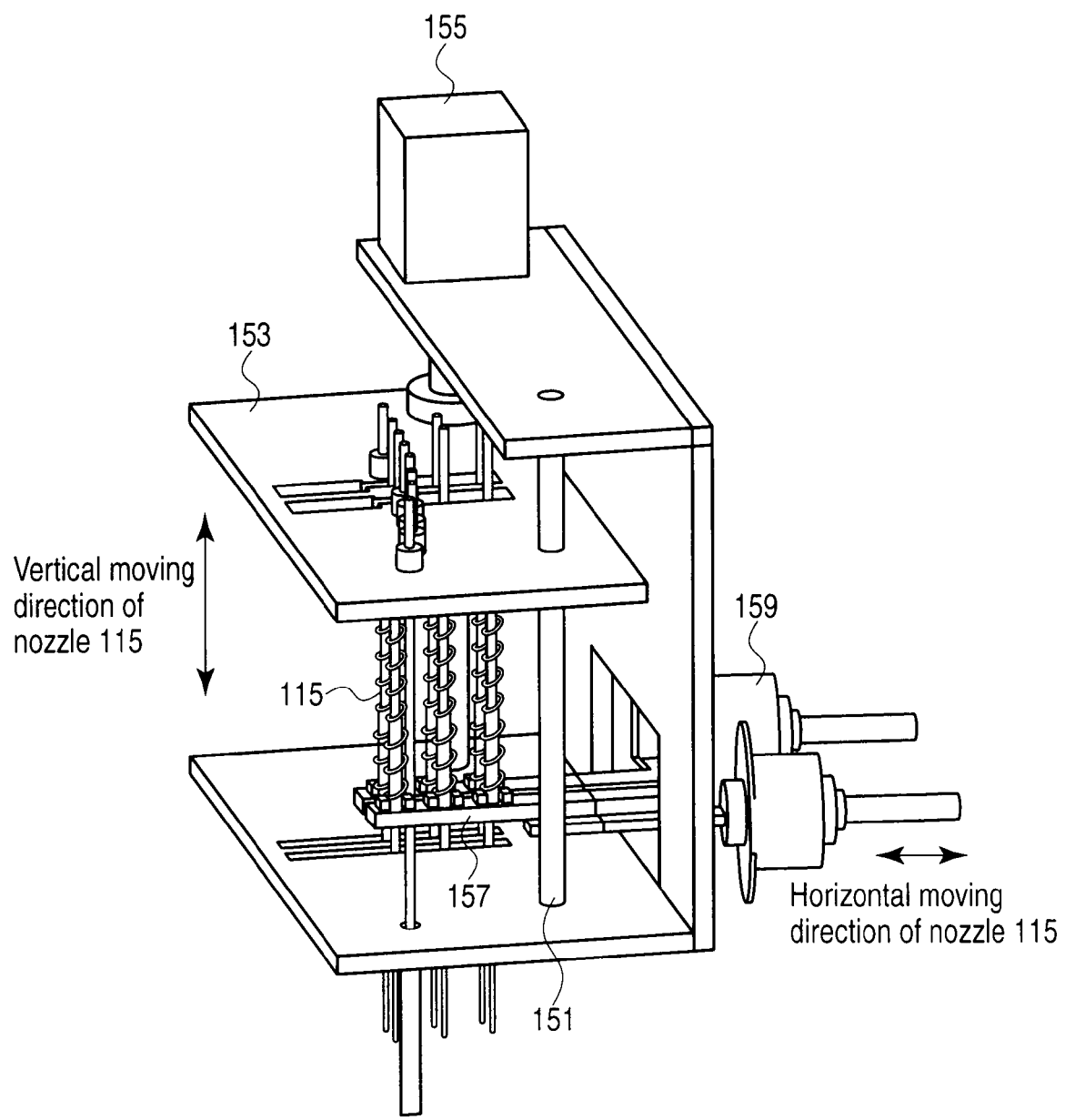
F I G. 14

| | Cleaning position a | Cleaning position b | Cleaning position c | Cleaning position d | Cleaning position e | Cleaning position f | Cleaning position g | Cleaning position h |
|---|---|---|---|---|---|---|---|---|
| Cleaning pattern F | OFF | Alkaline cleaner cleaning | Acidic cleaner cleaning | Water cleaning | Water cleaning | Water cleaning | Suction | Drying |
| Cleaning pattern G | OFF | OFF | OFF | OFF | OFF | OFF | OFF | OFF |

FIG. 16

| | Cleaning position a | Cleaning position b | Cleaning position c | Cleaning position d | Cleaning position e | Cleaning position f | Cleaning position g | Cleaning position h |
|---|---|---|---|---|---|---|---|---|
| Cuvette G | OFF | OFF | OFF | OFF | OFF | OFF | OFF | OFF |

FIG. 17

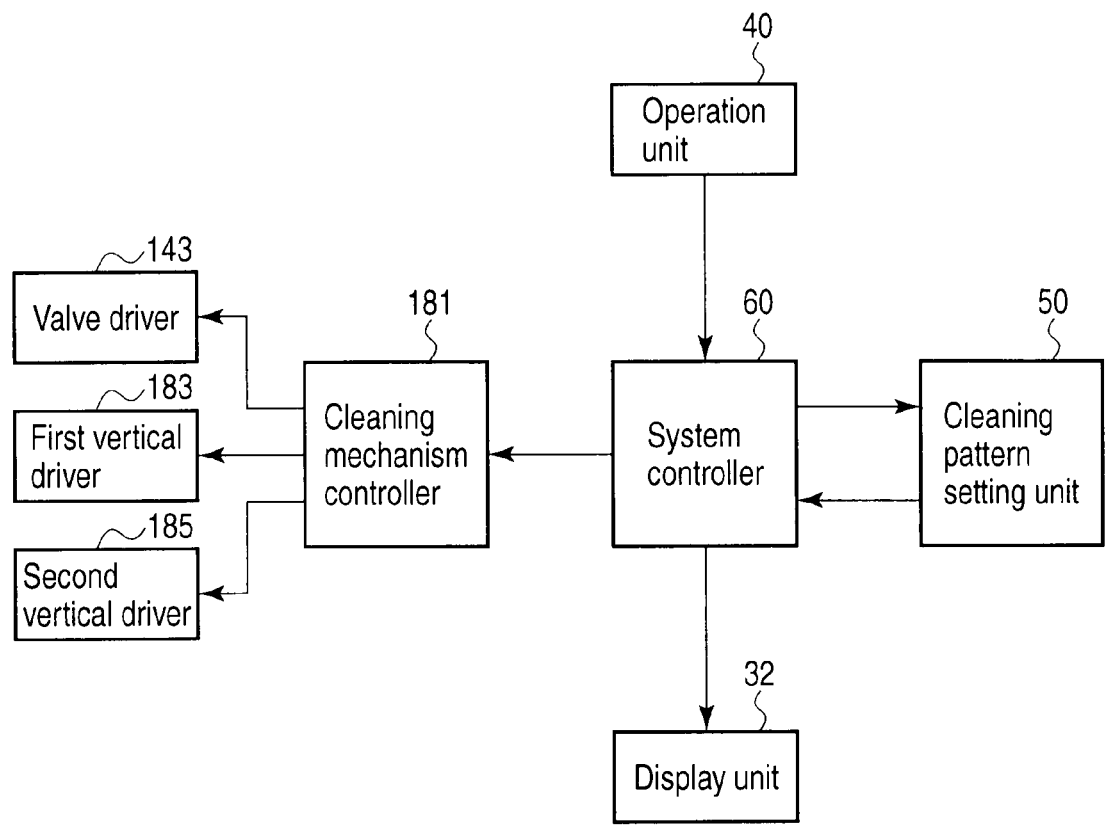
FIG.20
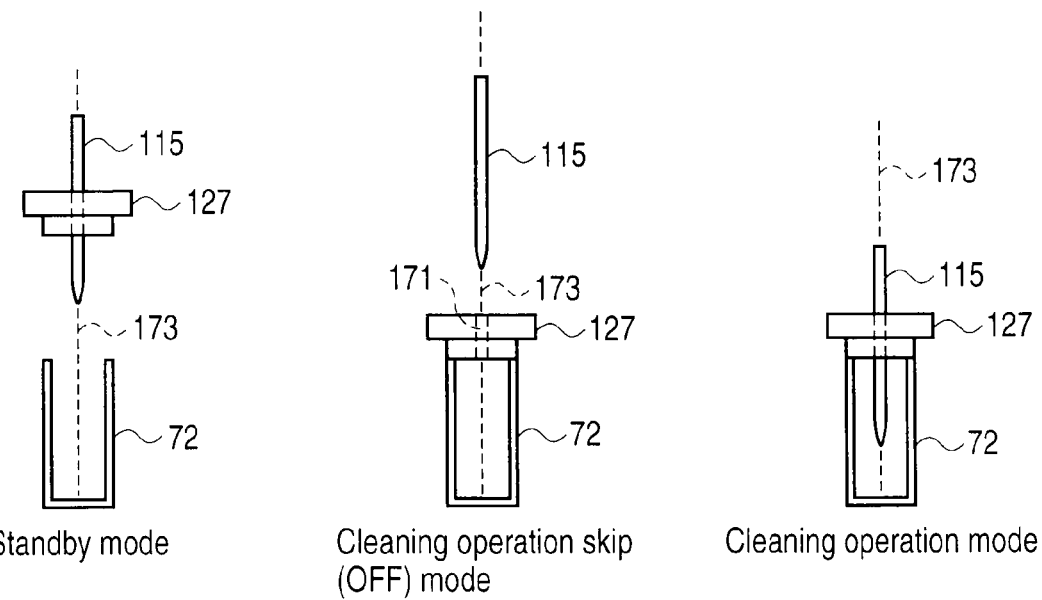
FIG.21 — Standby mode
FIG.22 — Cleaning operation skip (OFF) mode
FIG.23 — Cleaning operation mode

AUTOMATIC ANALYZER

CROSS-REFERENCE TO RELATED APPLICATIONS

This application is based upon and claims the benefit of priority from Japanese Patent Application No. 2010-085239, filed Apr. 1, 2010; the entire contents of which are incorporated herein by reference.

FIELD

Embodiments described herein relate generally to an automatic analyzer.

BACKGROUND

An automatic analyzer measures measurement items such as biochemical test items and immunological test items. The automatic analyzer dispenses a sample and reagent corresponding to each measurement item into a cuvette, and stirs them. When the sample and reagent are stirred, a mixed liquid causes a chemical reaction, for example, its color tone or turbidity changes. The automatic analyzer measures this change in color tone or turbidity by measuring a light transmission amount, thereby measuring the concentrations of various components and the activity of an enzyme in the sample. After measurement, the mixed liquid is disposed. Then, the cuvette of the mixed liquid is cleaned with a cleaner and water by cleaning nozzles, and is dried by a drying nozzle. The dried cuvette is used again in measurement.

Optimal cleaning patterns of the cuvette are different depending on measurement items, that is, samples and reagents. Note that the cleaning pattern specifies, for example, the types, the numbers of times of use, and the use order of cleaning liquids to be used. However, sharing roles of respective cleaning nozzles are fixed. That is, the cuvette is cleaned according to a given cleaning pattern irrespective of the types of samples and reagents. Therefore, the cuvette cannot often be cleaned according to a cleaning pattern optimal to a measurement item, and improvements of the cleaning precision and cleaning efficiency of the cuvette are demanded.

When the cleaning nozzle is inserted into or pulled out from the cuvette, for example, the cleaning liquid and mixed liquid contained in the cuvette are spattered from the cleaning nozzle, and often enter into another cuvette. Due to mixture of the cleaning liquid into the cuvette, the cleaning precision and cleaning efficiency of the cuvette deteriorate.

BRIEF DESCRIPTION OF THE DRAWINGS

FIG. 3 is a table showing examples of cleaning patterns set by a cleaning pattern setting unit in FIG. 1;

FIG. 4 is a table showing examples of cleaning patterns set to respective cuvettes by the cleaning pattern setting unit in FIG. 1;

FIG. 5 is a diagram illustrating the structure of the cleaning mechanism according to a first example of the first embodiment;

FIG. 8 is a table for explaining operation examples of the cleaning mechanism under the control of a cleaning mechanism controller shown in FIG. 7, and showing cuvettes allocated at respective cleaning positions for respective pivot cycles;

FIG. 10 is a perspective view of a module formed of nozzles and a cover according to the first modification of the first example;

FIG. 12 is a diagram illustrating the structure of the cleaning mechanism according to a second example of the first embodiment;

FIG. 13 is a schematic perspective view associated with the front surface direction of the cleaning mechanism shown in FIG. 12;

FIG. 14 is a schematic perspective view associated with the side surface direction of the cleaning mechanism shown in FIG. 12;

FIG. 16 is a table showing examples of cleaning patterns set by the cleaning pattern setting unit according to the second embodiment;

FIG. 17 is a table showing an example of a cleaning pattern set to each cuvette by the cleaning pattern setting unit according to the second embodiment;

FIG. 20 is a functional block diagram of a cleaning system of an automatic analyzer according to the second embodiment;

FIG. 21 is a view for explaining an operation example of the nozzle and cover under the control of a cleaning mechanism controller in FIG. 20, and showing the positional relationship among the nozzle, the cover, and a cuvette in a standby mode;

FIG. 22 is a view for explaining an operation example of the nozzle and cover under the control of the cleaning mechanism controller in FIG. 20, and showing the positional relationship among the nozzle, cover, and cuvette in a cleaning operation skip (OFF) mode;

FIG. 23 is a view for explaining an operation example of the nozzle and cover under the control of the cleaning mechanism controller in FIG. 20, and showing the positional relationship among the nozzle, cover, and cuvette in a cleaning operation mode;

DETAILED DESCRIPTION

In general, according to one embodiment, an automatic analyzer includes a reaction disc, cleaning mechanism, and cover. The reaction disc holds a cuvette which contains a sample and a reagent. The cleaning mechanism is configured to clean the cuvette using a nozzle. The cover is configured to be movable along an axis of the nozzle and to cover an opening of the cuvette.

The automatic analyzer according to this embodiment will be described hereinafter with reference to the drawings.

(First Embodiment)

Figure 1:
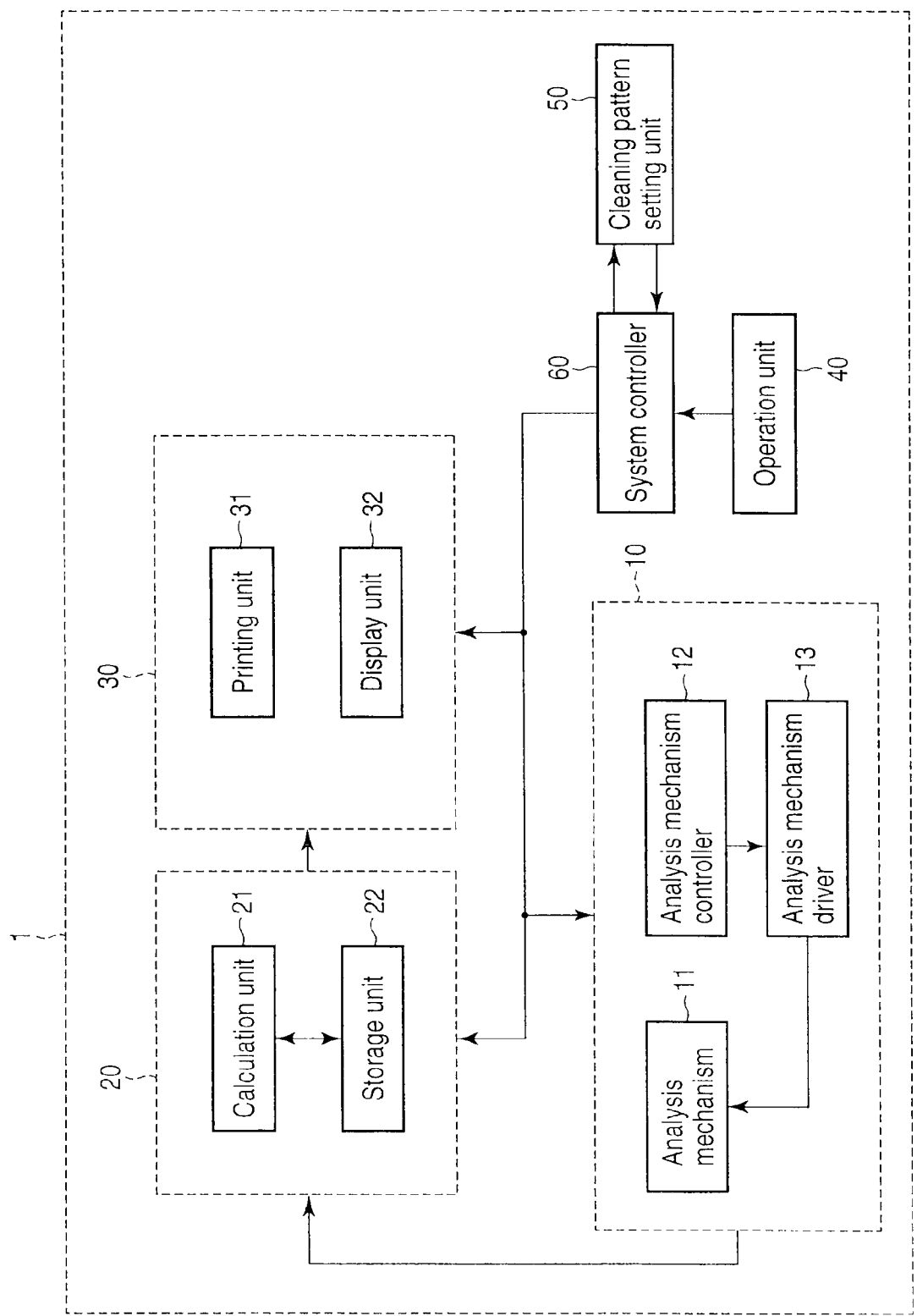
FIG. 1 is a block diagram showing the arrangement of an automatic analyzer according to the first embodiment.

FIG. 1 is a block diagram showing the arrangement of an automatic analyzer 1 according to the first embodiment. As shown in FIG. 1, the automatic analyzer 1 includes an analysis unit 10, data processor 20, output unit 30, operation unit 40, cleaning pattern setting unit 50, and system controller 60.

The analysis unit 10 measures a sample such as a blood serum or urine using a reagent for each measurement item, and generates measurement data associated with the sample. The analysis unit 10 includes an analysis mechanism 11, analysis mechanism controller 12, and analysis mechanism driver 13.

Figure 2:
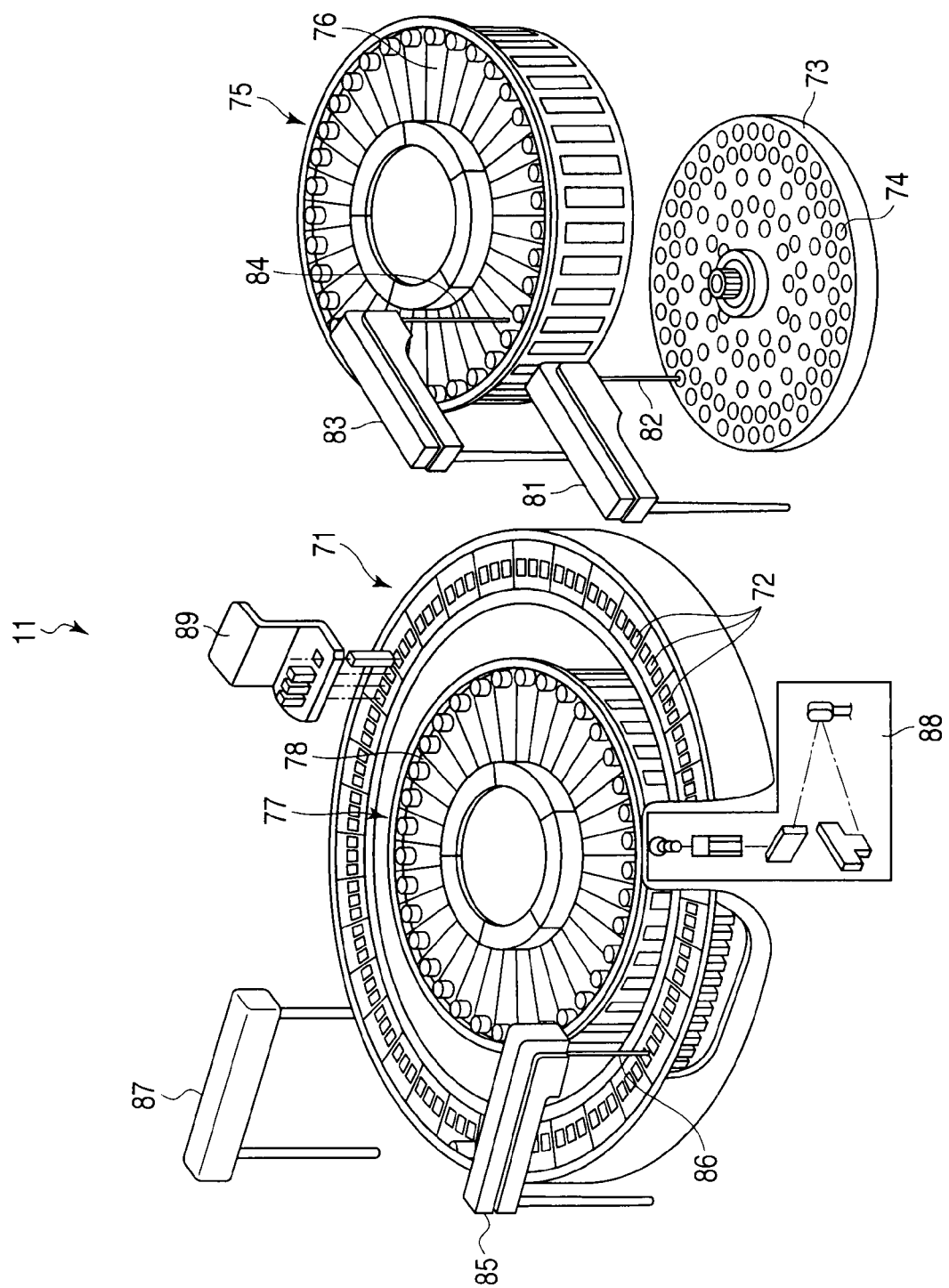
FIG. 2 is a perspective view showing the structure of an analysis mechanism in FIG. 1.

FIG. 2 is a perspective view showing the structure of the analysis mechanism 11. As shown in FIG. 2, the analysis mechanism 11 includes a reaction disc 71. The reaction disc 71 pivotally holds a plurality of (m) cuvettes 72 which are placed at equal angular intervals on the circumference. The reaction disc 71 alternately repeats a pivot action through a prescribed angle and a stop action for a predetermined period. In this case, a unit operation series including one pivot action and one stop action which follows will be referred to as a pivot cycle hereinafter. A pivot angle is specified according to, for example, a revolving cycle of the reaction disc 71. The revolving cycle is a unit operation series for placing each cuvette 72 on adjacent cuvette position. For example, the pivot angle corresponds to about ⅓ revolution. In this case, when the reaction disc 71 pivots three times, it pivots by one revolution and one cuvette position. In other words, each cuvette 72 moves by one cuvette position for each revolving cycle. When the revolving cycles as many as the number of cuvette positions of the reaction disc 71 are repeated, each cuvette 72 returns to a former cuvette position. For example, when the reaction disc 71 has 40 cuvette positions, 40 revolving cycles have to be repeated so as to return each cuvette 72 to the former cuvette position. A unit operation series from the beginning of pivot actions of the cuvettes 72 until the cuvettes 72 are placed at all cuvette positions in turn and are returned to their former cuvette positions will be referred to as an analysis cycle hereinafter.

The analysis mechanism 11 has a disc sampler 73 in the vicinity of the reaction disc 71. The disc sampler 73 pivotally holds sample vessel 74. Each sample vessel 74 contains a sample such as a standard sample or subject's sample. The analysis mechanism 11 has a first reagent reservoir 75 in the vicinity of the reaction disc 71. The first reagent reservoir 75 pivotally holds first reagent bottle 76. Each first reagent bottle 76 contains a first reagent which reacts with a component of each measurement item contained in a sample. The analysis mechanism 11 has a second reagent reservoir 77 on the inner periphery side of the reaction disc 71. The second reagent reservoir 77 pivotally holds second reagent bottles 78. Each second reagent bottle 78 contains a second reagent corresponding to the first reagent.

The analysis mechanism 11 includes a sample arm 81 between the reaction disc 71 and disc sampler 73. The sample arm 81 pivotally and vertically movably supports a sample probe 82. The sample probe 82 suctions a sample from a sample vessel 74 located at a sample suction position on the disc sampler 73, and discharges the sample into a cuvette 72 located at a sample discharge position on the reaction disc 71.

The analysis mechanism 11 includes a first reagent arm 83 between the reaction disc 71 and first reagent reservoir 75. The first reagent arm 83 pivotally and vertically movably supports a first reagent probe 84. The first reagent probe 84 suctions a first reagent from a first reagent bottle 76 located at a first reagent suction position on the first reagent reservoir 75, and discharges the first reagent into a cuvette 72 located at a first reagent discharge position on the reaction disc 71. The analysis mechanism 11 includes a second reagent arm 85 in the vicinity of the reaction disc 71. The second reagent arm 85 pivotally and vertically movably supports a second reagent probe 86. The second reagent probe 86 suctions a second reagent from a second reagent bottle 78 located at a second reagent suction position on the second reagent reservoir 77, and discharges the second reagent into a cuvette 72 located at a second reagent discharge position on the reaction disc 71.

The analysis mechanism 11 has an stirring mechanism 87, photometry mechanism 88, and cleaning mechanism 89. The stirring mechanism 87 stirs a mixed liquid of a sample and first reagent or that of a sample, first reagent, and second reagent in a cuvette 72 located at a stirring position on the reaction disc 71 using a stirrer. The photometry mechanism 88 irradiates a cuvette 72 pivoted by the reaction disc 71 with light (measurement beam). And the photometry mechanism 88 converts light transmitted through a mixed liquid containing a sample into an absorbency to generate measurement data. The photometry mechanism 88 outputs the generated measurement data to the data processor 20.

The cleaning mechanism 89 cleans a plurality of cuvettes 72 respectively placed at a plurality of cleaning positions on the reaction disc 71 using cleaning nozzles. Also, the cleaning mechanism 89 dries a cleaned cuvette 72 using a drying nozzle. More specifically, the cleaning mechanism 89 cleans a cuvette 72 to be cleaned according to a cleaning pattern corresponding to a measurement item of a sample in that cuvette 72 to be cleaned. The cleaning pattern can be set to each measurement item. The cleaning pattern can be arbitrary set according to a user's instruction via the operation unit 40.

The analysis mechanism controller 12 controls the analysis mechanism driver 13 so as to drive the respective mechanisms. More specifically, the analysis mechanism driver 13 respectively pivots the reaction disc 71, disc sampler 73, first reagent reservoir 75, and second reagent reservoir 77 under the control of the analysis mechanism controller 12. The analysis mechanism driver 13 respectively pivots and vertically moves the sample arm 81, first reagent arm 83, and second reagent arm 85 under the control of the analysis mechanism controller 12. The analysis mechanism driver 13 controls the cleaning mechanism 89 under the control of the analysis mechanism controller 12.

The analysis mechanism driver 13 drives a sample dispensing pump to cause the sample probe 82 to suction and discharge a sample under the control of the analysis mechanism controller 12. Also, the driver 13 drives a first reagent dispensing pump to cause the first reagent probe 84 to suction and discharge a first reagent under the control of the controller 12. The driver 13 drives a second reagent dispensing pump to cause the second reagent probe 86 to suction and discharge a second reagent under the control of the controller 12. The driver 13 drives a cleaning pump to cause each nozzle of the cleaning mechanism 89 to suction a mixed liquid in a cuvette 72, to discharge a cleaning liquid into the cuvette 72, and to suction the cleaning liquid in the cuvette 72 under the control of the controller 12. The driver 13 drives a dry pump to cause the drying nozzle of the cleaning mechanism 89 to dry the interior of a cuvette 72 under the control of the controller 12.

As described above, the reaction disc 71 alternately repeats pivot and stop actions for respective pivot cycles. The analysis mechanism controller 12 executes dispensing, stirring, photometry, and cleaning operations while repeating such pivot and stop actions. For example, the controller 12 executes the dispensing, cleaning, and stirring operations during a stop period of the reaction disc 71, and executes the photometry operation during a pivot period of the reaction disc 71.

The data processor 20 calculates and stores various data generated by the analysis unit 10. The data processor 20 includes a calculation unit 21 and storage unit 22. The calculation unit 21 generates calibration curves based on measurement data of respective measurement items generated by the photometry mechanism 88, stores data of the generated calibration curves in the storage unit 22, and supplies them to the output unit 30. Also, the calculation unit 21 generates analysis data such as the concentrations and activity values of measurement item components from the measurement data using the generated calibration curve data, stores the generated analysis data in the storage unit 22, and supplies the analysis data to the output unit 30. The storage unit 22 includes a storage medium such as a hard disc. The storage unit 22 stores calibration curve data generated by the calculation unit 21 for respective measurement items, and saves analysis data of respective measurement items for respective samples.

The output unit 30 outputs, for example, the calibration curves and analysis data generated by the data processor 20 in various modes. More specifically, the output unit 30 includes a printing unit 31 and display unit 32. As the printing unit 31, an output device such as a printer can be used. The printer prints, for example, the calibration curves and analysis data output from the data processor 20 onto a printer sheet in a predetermined layout. The display unit 32 displays the calibration curves and analysis data output from the data processor 20. Also, the display unit 32 displays an analysis condition setting screen used to set analysis conditions such as a liquid volume of a sample, that of a first reagent, that of a second reagent, and a wavelength of a measurement beam in association with each measurement item, and a sample information setting screen used to set a sample ID, sample name, and the like. The display unit 32 also displays, for example, a measurement item selection screen used to select a measurement item for each sample, and a cleaning pattern setting screen used to set a cleaning pattern for each measurement item. As the display unit 32, display devices such as a CRT (cathode-ray tube) display, liquid crystal display, organic EL (electro luminescence) display, and plasma display can be used as needed.

The operation unit 40 is used to input analysis conditions of respective measurement items, and various command signals. More specifically, the operation unit 40 includes input devices such as a keyboard, mouse, various buttons, and touch key panel. The operation unit 40 inputs measurement items to be measured, analysis conditions of the respective measurement items, patient information (for example, patient IDs and patient names), and cleaning patterns of the respective measurement items according to user's instructions via the input devices.

The setting unit 50 sets cleaning patterns according to user's instructions associated with cleaning patterns input via the operation unit 40.

The system controller 60 systematically controls the respective units included in the automatic analyzer 1 so as to perform measurements associated with measurement items. As a characteristic technique of this embodiment, the system controller 60 controls the respective units according to cleaning patterns set for respective measurement items.

Cleaning pattern setting processing by the setting unit 50 will be described below. FIG. 3 is a table showing examples of cleaning patterns set by the setting unit 50. As shown in FIG. 3, each cleaning pattern is specified by cleaning operations at respective cleaning positions on the reaction disc 71. The cleaning operations include, for example, ejection of a high-concentration waste liquid, ejection of low-concentration waste liquid, cleaning using pure water, cleaning using an alkaline cleaner, that using an acidic cleaner, suction, and drying. In ejection of a high- or low-concentration waste liquid, and cleaning using pure water, pure water is discharged from a nozzle into a cuvette 72, after a waste liquid in a cuvette 72 is suctioned by a nozzle and ejected. In cleaning using an alkaline cleaner, the alkaline cleaner is discharged from a nozzle into a cuvette 72, after a waste liquid in a cuvette 72 is suctioned by a nozzle and ejected. In cleaning using an acidic cleaner, the acidic cleaner is discharged from a nozzle into a cuvette 72, after a waste liquid in a cuvette 72 is suctioned by a nozzle and ejected.

Each cuvette 72 is located in turn from cleaning position a to cleaning position h for respective revolving cycles, and is cleaned at each cleaning position. That is, the cleaning positions mean the order of the cleaning operations of the cuvette 72. For example, in cleaning pattern A, at position a, pure water is injected into a cuvette 72, and a high-concentration waste liquid is ejected from the cuvette 72. Next, at position b, the cuvette 72 is cleaned using an alkaline cleaner. At position c, the cuvette 72 is cleaned using an acidic cleaner. At position d, the cuvette 72 is cleaned using pure water. At position e, the cuvette 72 is cleaned using pure water. At position f, the cuvette 72 is cleaned using pure water. At position g, a liquid such as the pure water is suctioned from the cuvette 72. At position h, the cuvette 72 is dried.

Since the cleaning operations are specified for respective cleaning positions, as shown in FIG. 3, cleaning water of the same type can be used at a plurality of cleaning positions. For example, cleaning using an alkaline cleaner can be executed at both cleaning positions b and c like cleaning pattern B. Also, cleaning using an acidic cleaner can be executed at both cleaning positions b and c like cleaning pattern E.

The cleaning patterns are set, for example, after measurement items are set. Upon setting of a cleaning pattern, the user selects one of these plurality of specified cleaning patterns for each measurement item via the operation unit 40. The setting unit 50 sets the selected cleaning pattern for a measurement item as a setting target. Each measurement item and cuvette 72 are associated with each other by, for example, the system controller 60. The setting unit 50 sets the set cleaning pattern for a cuvette 72 used in measurement of the measurement item as the setting target. Therefore, by setting the cleaning pattern for the measurement item, the cuvette 72 used in measurement of that measurement item is cleaned according to the cleaning pattern set for that measurement item.

FIG. 4 is a table showing examples of cleaning patterns set to respective cuvettes 72 by the setting unit 50. As can be seen from comparison between FIGS. 3 and 4, arbitrary one of existing cleaning patterns is assigned to each cuvette 72 (cuvettes A, B, C, D, E, F, and G in FIG. 4). For example, cleaning pattern A in FIG. 3 is set to cuvette A.

Note that the cleaning patterns are specified in advance in the above description. However, this embodiment is not limited to this. For example, the setting unit 50 may set cleaning operations for respective cleaning positions in association with each measurement item according to user's instructions via the operation unit 40. Also, the setting unit 50 may change cleaning operations of a cleaning pattern according to user's instructions via the operation unit 40.

Next, arrangements and operations required to attain such cleaning operations will be described in detail below separately in first and second examples.

FIRST EXAMPLE

FIG. 5 illustrates the structure of the cleaning mechanism 89 according to a first example of the first embodiment. As shown in FIG. 5, the cleaning mechanism 89 has a plurality of cleaning liquid containers such as a pure water tank 101, alkaline cleaner tank 103, and acidic cleaner tank 105. The pure water tank 101 stores pure water as one of cleaning liquids. To the pure water tank 101, a pure water line 107 as a channel of the pure water is connected. The pure water line 107 connects the pure water tank 101 and a channel switching valve 113. The alkaline cleaner tank 103 stores an alkaline cleaner as one of the cleaning liquids. To the alkaline cleaner tank 103, an alkaline cleaner line 109 as a channel of the alkaline cleaner is connected. The alkaline cleaner line 109 connects the alkaline cleaner tank 103 and channel switching valve 113. The acidic cleaner tank 105 stores an acidic cleaner as one of the cleaning liquids. To the acidic cleaner tank 105, an acidic cleaner line 111 as a channel of the acidic cleaner is connected. The acidic cleaner line 111 connects the acidic cleaner tank 105 and channel switching valve 113.

At a plurality of cleaning positions a to h on the reaction disc 71, a plurality of nozzles 115 are respectively arranged. That is, one nozzle 115 is arranged per cleaning position. The plurality of nozzles 115 are supported by a vertical support mechanism (not shown) to be individually movable in the vertical direction. The nozzles 115 at positions a to f are used for cleaning using cleaning liquids. The nozzle 115 at position g is used for suctioning. The nozzle 115 at position h is used for suctioning and drying by means of a dry tip 117.

To the plurality of nozzles 115, a plurality of supply channels (to be referred to as supply lines hereinafter) 119 are respectively connected. The plurality of supply lines 119 connect the plurality of nozzles 115 and channel switching valve 113. In each supply line 119, the pure water, alkaline cleaner, or acidic cleaner to be discharged into a cuvette 72 selectively flows for each pivot cycle.

To the plurality of nozzles 115, a plurality of ejection channels (to be referred to as ejection lines hereinafter) are connected. The ejection lines include a high-concentration waste liquid line 121, low-concentration waste liquid lines 123, and suction lines 125. The line 121 is a channel for a relatively high-concentration waste liquid. For example, the line 121 is connected to the nozzle 115 at position a. The lines 123 are channels for a relatively low-concentration waste liquid. For example, the lines 123 are connected to the nozzles 115 at cleaning positions b to f. The lines 125 are channels for moisture (due to, for example, the pure water) in cuvettes 72. For example, the lines 125 are connected to the nozzles 115 at cleaning positions g and h.

The channel switching valve 113 is a mechanism which changes over connections between the respective nozzles 115 (the supply lines 119) and the respective cleaner lines (the pure water line 107, alkaline cleaner line 109, and acidic cleaner line 111). The channel switching valve 113 changes over the connections between the respective nozzles 115 and respective cleaner lines so as to cause cleaning liquids according to a cleaning pattern to flow in the respective nozzles 115. The channel switching valve 113 is configured by, for example, an electromagnetic valve. The channel switching valve 113 is actuated upon reception of a drive signal from a valve driver (to be described later). The channel switching valve 113 can simultaneously connect one cleaning line to the plurality of nozzles 115 (supply lines 119). For example, the pure water line 107 can be simultaneously connected to the supply lines 119 at cleaning positions c, d, and e.

Figure 6:
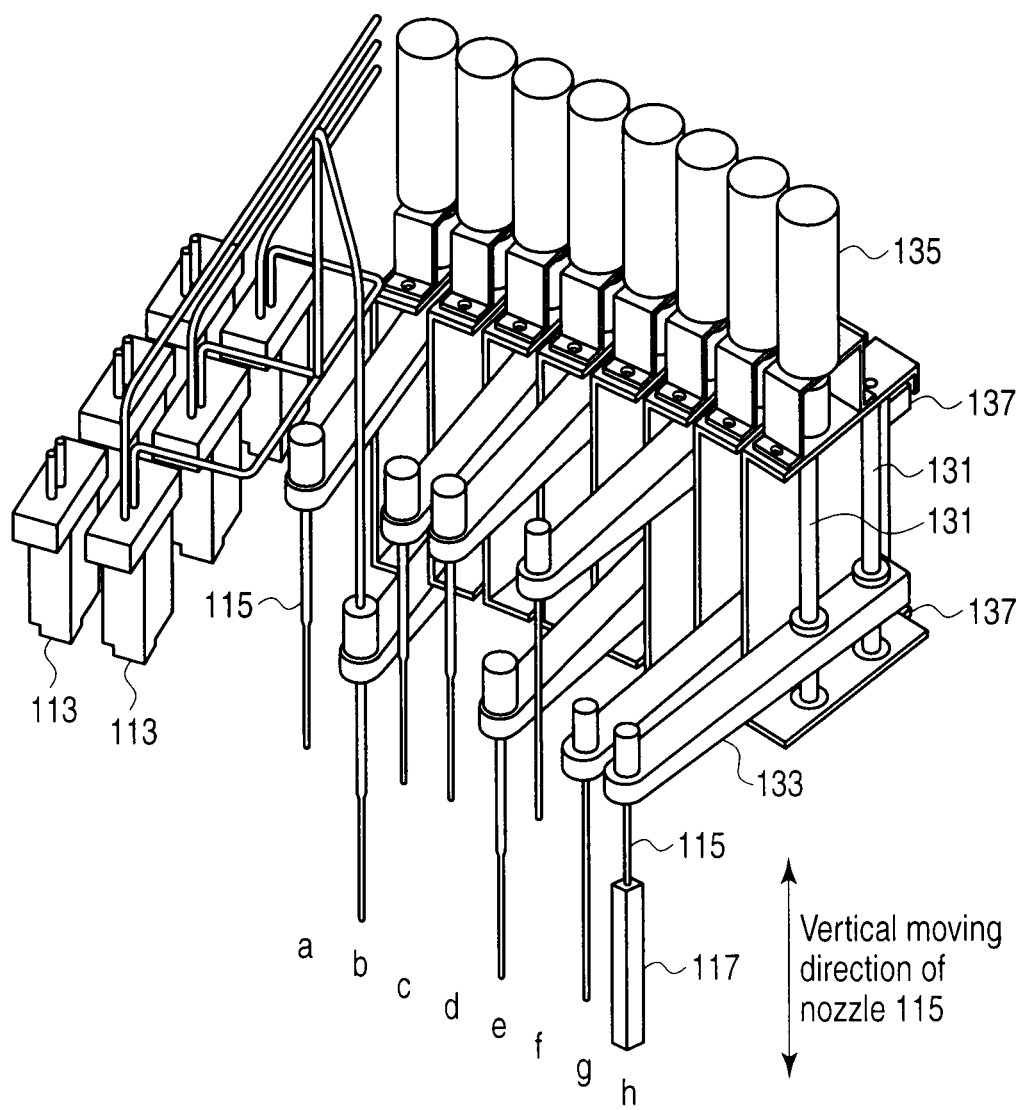
FIG. 6 is a schematic perspective view showing the structure of the cleaning mechanism in FIG. 5.

The structure of the cleaning mechanism 89 according to the first example will be described below. FIG. 6 is a schematic perspective view showing the structure of the cleaning mechanism 89 according to the first example. As shown in FIG. 6, the cleaning mechanism 89 has a structure which can individually move the plurality of nozzles 115 vertically. More specifically, the cleaning mechanism 89 has a plurality of lead screws 131. Each lead screw 131 is typically a columnar structure on the surface of which a spiral groove is formed. Each lead screw 131 is fixed, so that its axial center extends substantially along the vertical direction. Arms 133 are attached to the lead screws 131. Through holes are formed in one end of each arm 133. On the inner surface of each through hole, a groove fitted with that on the surface of the lead screw 131 is formed. Each arm 133 is threadably mounted on the lead screws 131 in the through holes. In this way, the lead screws 131 serve as a vertical support mechanism which supports the arms 133 to be vertically movable in substantially the vertical direction. The nozzle 115 is attached to the other end of each arm 133. A DC motor (DC electric motor drive) 135 is arranged on one end of each lead screw 131. The DC motor 135 serves as a vertical driver. The DC motors 135 are driven under the control of a cleaning mechanism controller 141 (to be described later) to pivot the lead screws 131, thereby vertically moving the nozzles 115 in the vertical direction.

Photosensors 137 are attached to two ends of each lead screw 131. The photosensors 137 optically detect that the arm 133 reaches the end portion of the lead screw 131. When the photosensors 137 detect that the arm 133 reaches the end portion, the DC motor 135 is stopped.

Figure 7:
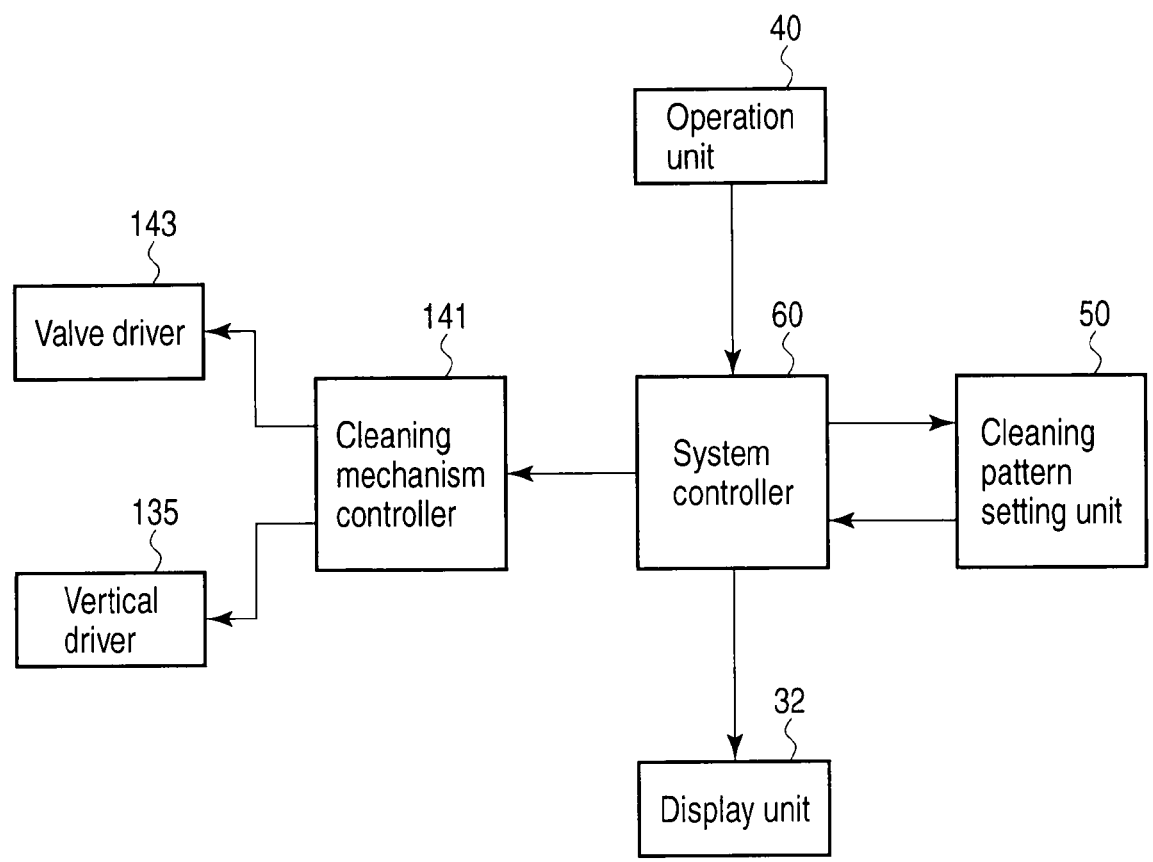
FIG. 7 is a functional block diagram of a cleaning system of the automatic analyzer according to the first example.

FIG. 7 is a functional block diagram of a cleaning system of the automatic analyzer 1 according to the first example of this embodiment. As shown in FIG. 7, the cleaning system of the automatic analyzer 1 includes the display unit 32, the operation unit 40, the setting unit 50, a cleaning mechanism controller 141, a vertical driver (DC motors) 135, and a valve driver 143 to have the system controller 60 as a core. Note that since the display unit 32, operation unit 40, and setting unit 50 have already described above, a description thereof will not be repeated.

The controller 141 is a part of the aforementioned analysis mechanism controller 12. The controller 141 controls the valve driver 143 and vertical driver 135 according to a cleaning pattern set by the setting unit 50. The valve driver 143 is a part of the aforementioned analysis mechanism driver 13. The valve driver 143 is driven under the control of the controller 141 to actuate the channel switching valve 113, thereby changing over the connections between the cleaning lines and nozzles 115. More specifically, the controller 141 actuates the channel switching valve 113 so that a cleaning liquid according to a cleaning operation set to a cuvette 72 to be cleaned is supplied to the nozzle 115 located at the cleaning position. The vertical driver 135 is a part of the aforementioned analysis mechanism driver 13. The vertical driver 135 is driven under the control of the controller 141 to actuate the vertical support mechanism (lead screws) 131, thereby vertically moving the nozzles 115.

An operation example of the cleaning mechanism 89 under the control of the cleaning mechanism controller 141 will be described in detail below. FIG. 8 is a table showing cuvettes 72 placed at respective cleaning positions for respective pivot cycles. As shown in FIG. 8, the revolving cycle includes n (for example, 3) pivot cycles, and the analysis cycle includes m (for example, 40) revolving cycles. Each cuvette 72 moves a cleaning position by one cuvette position for each revolving cycle. The cuvettes 72 are moved during a pivot period of the reaction disc 71, and are cleaned during a stop period of the reaction disc 71.

The controller 141 controls the valve driver 143 according to the cleaning patterns of cuvettes 72 placed at respective cleaning positions for each pivot cycle, and supplies cleaning liquids according to the cuvettes 72 at the respective cleaning positions to the nozzles 115. More specifically, the controller 141 identifies the cuvettes 72 placed at the respective cleaning positions for each pivot cycle. The cuvette placed at each cleaning position is identified by an existing technique. After the cuvettes 72 are identified, the controller 141 specifies cleaning patterns set to the identified cuvettes, and specifies cleaning operations at the cleaning positions of the specified cleaning patterns. Then, the controller 141 controls the valve driver 143 according to the specified cleaning operations to actuate the channel switching valve 113. The channel switching valve 113 is actuated by the valve driver 143 during, for example, the pivot period of the reaction disc 71 and an initial stage of the stop period of the reaction disc. When the specified cleaning operation is ejection of a high- or low-concentration waste liquid or water cleaning, the controller 141 controls the valve driver 143 to connect the pure water line 107 to the nozzle 115 at that cleaning position. On the other hand, when the specified cleaning operation is alkaline cleaner cleaning, the controller 141 controls the valve driver 143 to connect the alkaline cleaner line 109 to the nozzle 115 at that cleaning position. Also, when the specified cleaning operation is acidic cleaner cleaning, the controller 141 controls the valve driver 143 to connect the acidic cleaner line 111 to the nozzle 115 at that cleaning position.

Upon completion of the connections between the nozzles 115 and supply lines, the controller 141 controls the vertical driver 135 to move the nozzles 115 at the respective cleaning positions downward. Then, cleaning liquids according to the cuvettes 72 at the respective cleaning positions are discharged from the nozzles 115. For example, when the nozzle 115 and pure water line 107 are connected, pure water is discharged from that nozzle 115. When the nozzle 115 and alkaline cleaner line 109 are connected, an alkaline cleaner is discharged from that nozzle 115. When the nozzle 115 and acidic cleaner line 111 are connected, an acidic cleaner is discharged from that nozzle 115. After the cleaning liquids are discharged, the controller 141 controls the vertical driver 135 to move the nozzles 115 at the respective cleaning positions upward. After the nozzles 115 are moved upward, the reaction disc 71 is pivoted through the pivot angle. Then, actuation of the channel switching valve 113 and discharging of cleaning liquids are similarly repeated.

In this way, cleaning liquids according to the cleaning patterns set to the cuvettes 72 at the respective cleaning positions are discharged from the nozzles 115 at the respective cleaning positions under the control of the controller 141. For example, in a pivot cycle C1, the nozzle 115 at position a discharges a cleaning liquid corresponding to position a (first cleaning operation) in a cleaning pattern set to cuvette A. The nozzle 115 at position b discharges a cleaning liquid corresponding to position b (second cleaning operation) in a cleaning pattern set to cuvette B. The nozzle 115 at position c discharges a cleaning liquid corresponding to position c (third cleaning operation) in a cleaning pattern set to cuvette C. The nozzle 115 at position d discharges a cleaning liquid corresponding to position d (fourth cleaning operation) in a cleaning pattern set to cuvette D. The nozzle 115 at position e discharges a cleaning liquid corresponding to position e (fifth cleaning operation) in a cleaning pattern set to cuvette E. The nozzle 115 at position f discharges a cleaning liquid corresponding to position f (sixth cleaning operation) in a cleaning pattern set to cuvette F. The nozzle 115 at position g discharges a cleaning liquid corresponding to position g (seventh cleaning operation) in a cleaning pattern set to cuvette G. The nozzle 115 at position h discharges a cleaning liquid corresponding to position h (eighth cleaning operation) in a cleaning pattern set to cuvette H. Note that the nozzle 115 need not always discharge a cleaning liquid depending on the set cleaning operation.

Note that, for example, when an alkaline cleaner flows in the pivot cycle C1 and an acidic cleaner flows in a pivot cycle C2, cleaning liquids of different types flow through one supply line 119 between the different pivot cycles in some cases. In such case, the cleaning liquids of the different types are mixed with each other in the supply line 119, thus deteriorating the cleaning precision and degrading the supply line 119.

Prevention measures against deterioration of the cleaning precision and degradation of the supply line 119 will be described below. For example, the controller 141 supplies pure water to each supply line 119 for each pivot cycle independently of supply of a cleaning liquid for a cleaning operation, so as to clean the interior of that supply line 119. The pure water is preferably supplied until the residual alkaline cleaner or acidic cleaner inside the supply line 119 is pushed out from the nozzle 115. Note that the pure water used to clean the interior of the supply line 119 is preferably supplied after the end of supply of a cleaning liquid before the beginning of a pivotal motion of the reaction disc 71. Alternatively, the pure water may be supplied during the pivot period of the reaction disc 71. In this case, in order to prevent a liquid pushed out from the nozzle 115 from mixing into a cuvette during the pivot period, for example, the nozzle 115 is preferably retracted from the cleaning position. For example, a location where the nozzle 115 is to be retracted is preferably a cleaning pool formed to clean each supply line 119. Note that a liquid used to clean each supply line 119 is not limited to the pure water. For example, a cleaning liquid used by the supply line 119 to be cleaned in the next pivot cycle may be supplied to that supply line 119.

At the time of cleaning a cuvette 72 at each cleaning position, a liquid such as a cleaning liquid in the cuvette 72 may be spattered and may enter into another cuvette 72. In this case, the cleaning precision and measurement precision of the other cuvette 72 may deteriorate.

Prevention measures against such spattering of a liquid will be described below. As shown in FIG. 5, the vertical support mechanism 131 includes covers 127 used to cover openings of the cuvettes 72. Each cover 127 may be arranged to be vertically movable integrally with or independently of the nozzle 115. The following description will be given under the assumption that the cover 127 and nozzle 115 are integrally arranged. In this case, when the nozzle 115 is moved downward, the opening of the cuvette 72 is closed by the cover 127. That is, the cover 127 is fixed to a position of the nozzle 115 where it can cover the opening of the cuvette 72 when the nozzle 115 is moved downward. The cover 127 has a distal end portion which can fit into the opening of the cuvette 72. The cuvette 72 is hermetically closed when the distal end portion fits into the opening. Therefore, the cuvette 72 can be cleaned while its opening is closed. Then, a liquid such as a cleaning liquid can be prevented from being spattered to cuvettes 72 placed at other cleaning positions.

After an elapse of one analysis cycle, the measurement of a measurement item is complete. Therefore, after the elapse of one analysis cycle, the cleaning pattern set to a given cuvette 72 is cleared by the setting unit 50. When a new measurement item is to be measured in the next analysis cycle, the setting unit 50 sets a cleaning pattern associated with this new measurement item for a cuvette 72. Then, that cuvette 72 undergoes the dispensing, photometry, stirring, and cleaning operations while being pivoted by the reaction disc 71.

As described above, the automatic analyzer 1 according to the first example can set a cleaning pattern (the types, the order, and the numbers of times of use of cleaning liquids) of a cuvette 72, which undergoes a measurement of a given measurement item for each measurement item. The automatic analyzer 1 includes the channel switching valve 113 which changes over the connections between the cleaner lines (pure water line 107, alkaline cleaner line 109, and acidic cleaner line 111) and the nozzles 115. The automatic analyzer 1 drives the channel switching valve 113 to clean each cuvette 72 using the set cleaning pattern. With this arrangement, the automatic analyzer 1 according to the first example can change cleaning operations for respective cleaning positions for each pivot cycle. Therefore, the automatic analyzer 1 can clean a cuvette 72 using a cleaning pattern suited to each individual measurement item. In this way, the automatic analyzer 1 according to the first example can improve the cleaning efficiency of cuvettes 72.

FIRST MODIFICATION OF FIRST EXAMPLE

In the above embodiment, one nozzle is arranged per cleaning position. However, the first example is not limited to this. For example, nozzles as many as the number of types of cleaning liquids may be arranged per cleaning position. The cleaning mechanism 89 with such structure according to a first modification of the first example will be described below. In the following description, the same reference numerals denote components having substantially the same functions as those in the first example, and a repetitive description will be allowed only when it is required.

Figure 9:
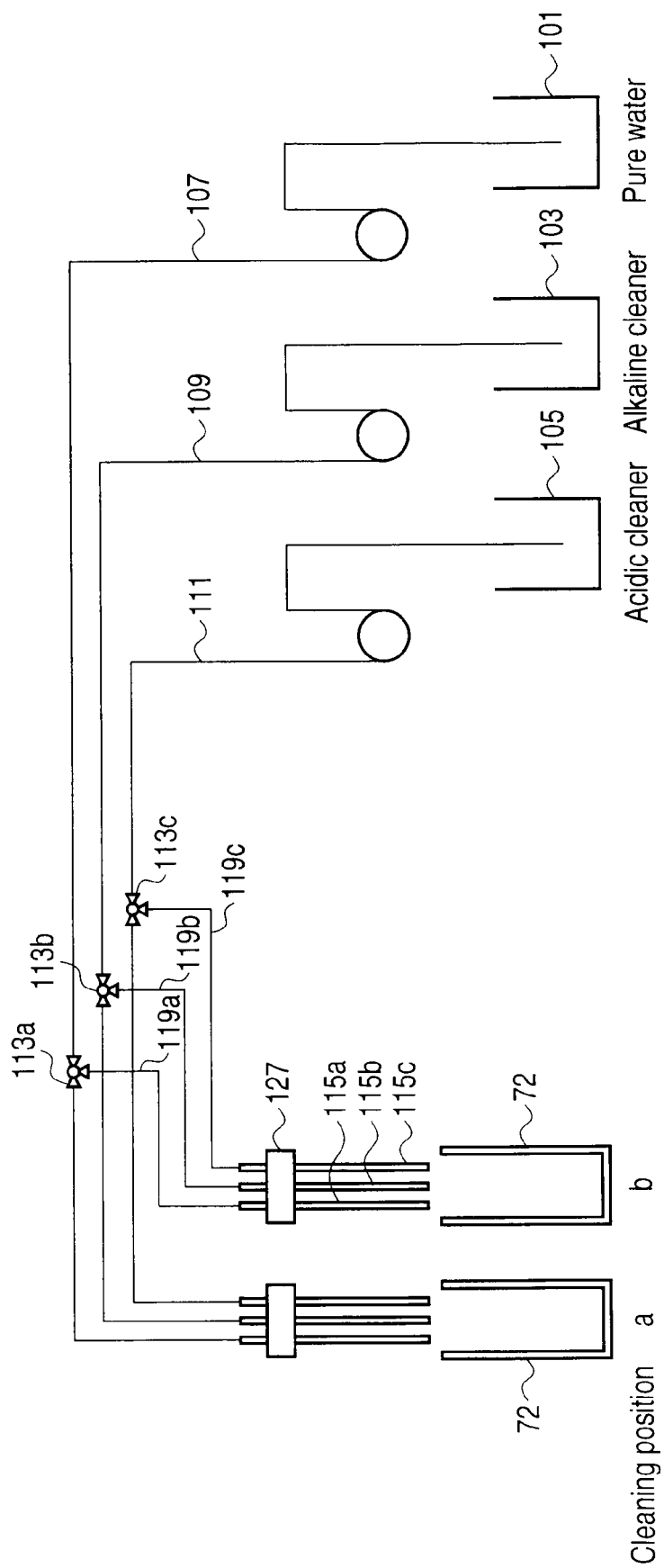
FIG. 9 is a diagram illustrating the structure of the cleaning mechanism according to a first modification of the first example.

FIG. 9 is a diagram illustrating the structure of the cleaning mechanism 89 according to the modification of the first example. As shown in FIG. 9, three nozzles 115 (a pure water nozzle 115a, alkaline cleaner nozzle 115b, and acidic cleaner nozzle 115c) are arranged at each cleaning position. These three nozzles 115 are attached to, for example, the cover 127. In this way, the three nozzles 115 and cover 127 form a module. The three nozzles are supported by a vertical support mechanism (not shown) to be integrally vertically movable. The pure water line 107 is connected to a channel switching valve 113a for pure water. The channel switching valve 113a and the nozzle 115a at each cleaning position are connected to a supply line 119a for pure water. The alkaline cleaner line 109 is connected to a channel switching valve 113b for an alkaline cleaner. The channel switching valve 113b and the nozzle 115b at each cleaning position are connected to a supply line 119b for an alkaline cleaner. The acidic cleaner line 111 is connected to a channel switching valve 113c for an acidic cleaner. The channel switching valve 113c and the nozzle 115c at each cleaning position are connected to a supply line 119c for an acidic cleaner.

The controller 141 controls the valve driver 143 according to a cleaning pattern set to a cuvette 72 placed at each cleaning position, and actuates the channel switching valves 113a, 113b, and 113c, so as to supply a cleaning liquid according to the cleaning pattern into the cuvette 72 at that cleaning position. After the channel switching valves 113 are actuated to switching the channels, the controller 141 controls a support mechanism driver 145 to move the nozzles 115a, 115b, and 115c downward together. The nozzles 115a, 115b, and 115c of the three types at each cleaning position are always vertically moved together irrespective of the types of cleaning liquids.

FIG. 10 is a perspective view of a module which includes a plurality of nozzles 115 (a pure water nozzle 115a, alkaline cleaner nozzle 115b, acidic cleaner nozzle 115c, and suction nozzle 115d) and the cover 127. As shown in FIG. 10, the four nozzles 115 are fixed to the cover 127. The plurality of nozzles 115 are preferably fixed to the cover 127 to be in tight contact with each other, so that they can enter into a cuvette 72 together.

SECOND MODIFICATION OF FIRST EXAMPLE

In the aforementioned embodiment, the cleaning mechanism 89 equips an independent driving mechanism which can independently vertically move the plurality of nozzles 115 arranged at the plurality of cleaning positions. However, this embodiment is not limited to this. For example, the cleaning mechanism 89 according to the second modification may equip a mechanism which can vertically move the plurality of nozzles 115 together. The automatic analyzer according to the second modification will be described below. In the following description, the same reference numerals denote components having substantially the same functions as those in the first embodiment, and a repetitive description will be allowed only when it is required.

Figure 11:
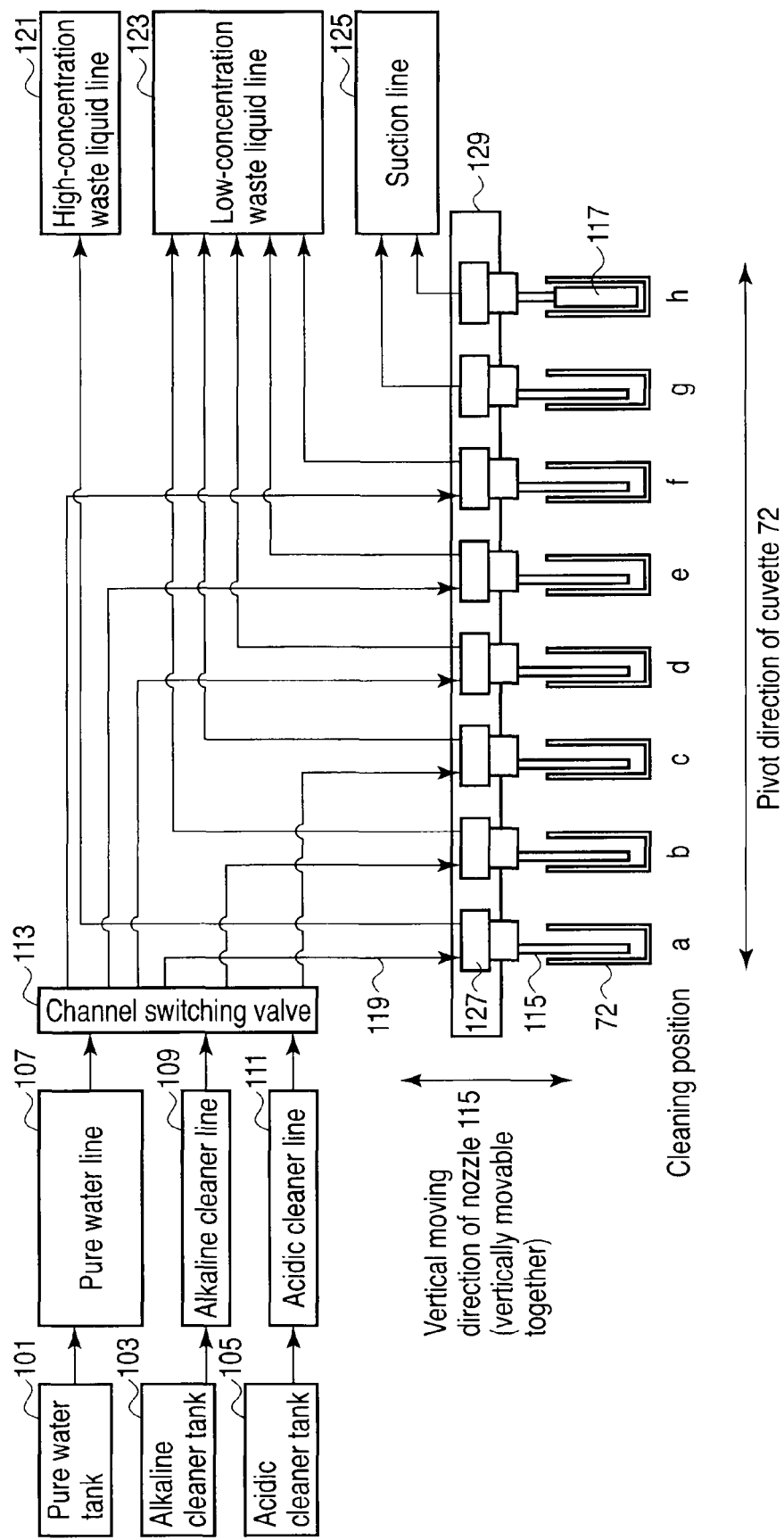
FIG. 11 is a diagram illustrating the structure of the cleaning mechanism according to a second modification of the first example.

FIG. 11 is a diagram illustrating the structure of the cleaning mechanism 89 according to the second modification. As shown in FIG. 11, the cleaning mechanism 89 according to the second modification has a vertical support mechanism 129 which supports the plurality of nozzles 115 at the plurality of cleaning positions to be vertically movable together in the vertical direction. The plurality of nozzles 115 are driven by the vertical driver 135 to be vertically moved together in the vertical direction.

SECOND EXAMPLE

As described above, the first example changes over the channel switching valve 113 according to a cleaning pattern. However, this embodiment is not limited to this. In the second example, a plurality of nozzles are arranged per cleaning position, and are horizontally moved according to a cleaning pattern to mechanically select a nozzle to be used. The automatic analyzer according to the second example will be described below.

FIG. 12 is a diagram illustrating the structure of the cleaning mechanism 89 according to the second example of this embodiment. Note that FIG. 12 illustrates only a mechanism associated with one cleaning position for the sake of simplicity. In practice, the cleaning mechanism 89 according to the second example includes a mechanism associated with a plurality of cleaning positions like in the first example.

As shown in FIG. 12, a plurality of nozzles 115 (a pure water nozzle 115a, alkaline cleaner nozzle 115b, and acidic cleaner nozzle 115c) according to the types of cleaning liquids are arranged at each cleaning position in correspondence with their functions. To the nozzle 115a, the pure water line 107 is connected. To the nozzle 115b, the alkaline cleaner line 109 is connected. To the nozzle 115c, the acidic cleaner line 111 is connected. Also, ejection lines (for example, low-concentration waste liquid lines 123) are connected to the plurality of nozzles 115.

The plurality of nozzles 115 are supported by a vertical support mechanism (not shown in FIG. 12) to be independently movable in the vertical direction. Also, the plurality of nozzles 115 are supported by a horizontal support mechanism (not shown in FIG. 12) to be movable in the horizontal direction.

The structure of the cleaning mechanism 89 according to the second example will be described below. FIG. 13 is a schematic perspective view associated with the front surface direction of the cleaning mechanism 89 according to the second example. FIG. 14 is a schematic perspective view associated with the side surface direction of the cleaning mechanism 89 according to the second example. As shown in FIGS. 13 and 14, the cleaning mechanism 89 according to the second example has a structure which can horizontally move the plurality of nozzles 115 arranged at each cleaning position. More specifically, the cleaning mechanism 89 according to the second example includes lead screws 151 each formed with a spiral groove. Each lead screw 151 is fixed so that its axial center extends along substantially the vertical direction. A support plate 153 is attached to the lead screws 151. Through holes are formed on an end portion of the support plate 153. On the inner surface of each through hole, a groove fitted with that of the surface of the lead screw 151 is formed. The support plate 153 is threadably mounted on the lead screws 151 in these through holes. In this way, the lead screws 151 support the support plate 153 to be vertically movable in substantially the vertical direction. Also, the plurality of nozzles 115 are attached to the support plate 153. On one end of each lead screw 151, a stepping motor 155 for a vertical motion is connected. The stepping motor 155 serves as a vertical driver. The stepping motors 155 are driven under the control of a cleaning mechanism controller (to be described later) to pivot the lead screws 151, thereby vertically moving the nozzles 115 in the vertical direction.

Arms 157 are arranged in correspondence with respective cleaning positions. The plurality of nozzles 115 arranged at each cleaning position are attached to the arm 157. On one end of the arm 157, a stepping motor 159 for a horizontal motion is connected. The stepping motor 159 serves as a horizontal driver. Each stepping motor 159 is driven under the control of a cleaning mechanism controller 161 (to be described later) to translate the arm 157 in the horizontal direction, thereby horizontally moving the plurality of nozzles 115.

Figure 15:
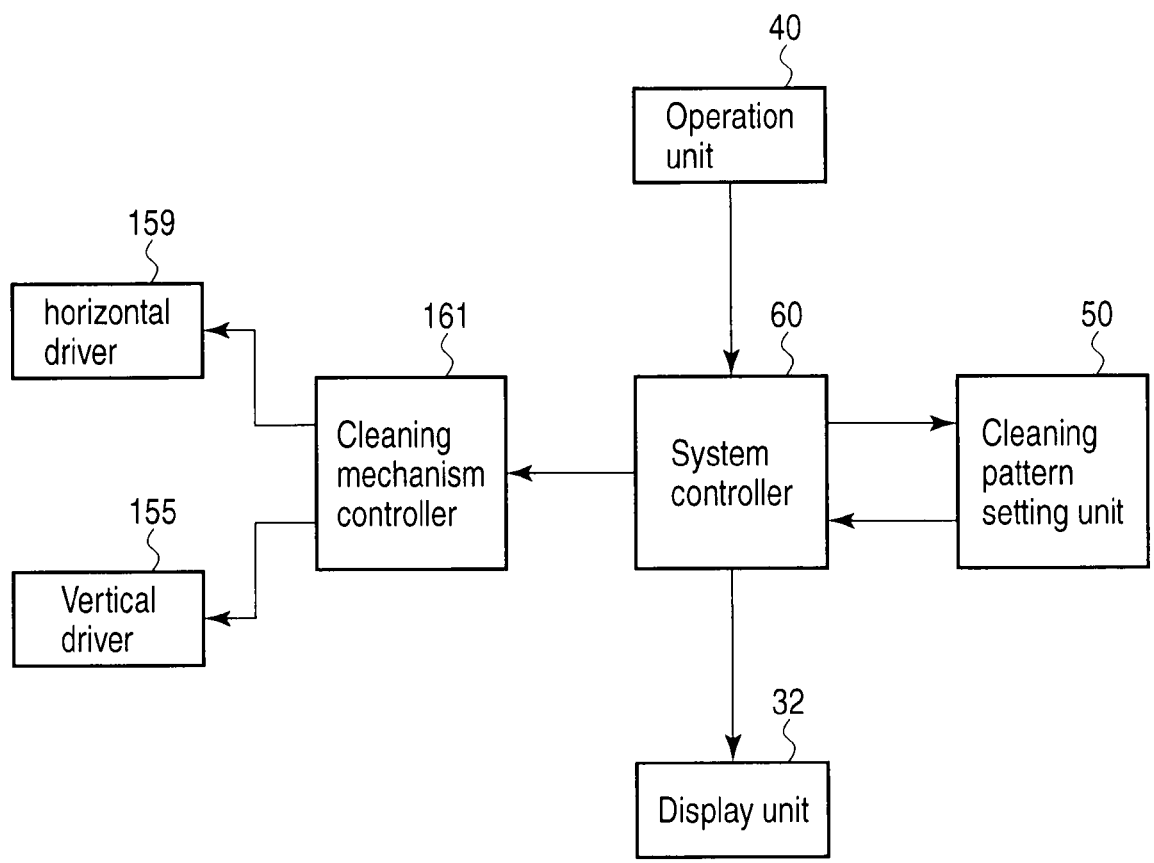
FIG. 15 is a functional block diagram of a cleaning system of the automatic analyzer according to the second example of the first embodiment.

FIG. 15 is a functional block diagram of a cleaning system of the automatic analyzer 1 according to the second example. As shown in FIG. 15, the cleaning system of the automatic analyzer 1 according to the second example has the display unit 32, the operation unit 40, the setting unit 50, a vertical driver 155, a horizontal driver 159, and a cleaning mechanism controller 161 to have the system controller 60 as a core. Note that the display unit 32, operation unit 40, and setting unit 50 have already been described previously, and a description thereof will not be repeated.

The controller 161 is a part of the aforementioned analysis mechanism controller 12. The controller 161 controls the horizontal driver (stepping motors for a horizontal motion) 159 and the vertical driver (stepping motors for a vertical motion) 155 in accordance with a cleaning pattern set to a cuvette 72 placed at each cleaning position. The horizontal driver 159 translates the nozzles 115 in the horizontal direction under the control of the controller 161 to locate the nozzle 115 for a cleaning liquid to a cleaning position according to the cleaning pattern of the cuvette 72 placed at the cleaning position. More specifically, the controller 161 locates the nozzle 115 for a cleaning liquid to a cleaning position according to a cleaning operation set to the cuvette 72 to be cleaned of the plurality of nozzles 115 arranged at each cleaning position. In this manner, the nozzle 115 according to the cleaning pattern of the cuvette 72 placed at each cleaning position can be mechanically selected. The vertical driver 155 vertically moves the nozzles 115 in the vertical direction under the control of the controller 161.

An operation example of the cleaning mechanism 89 under the control of the controller 161 will be described below. The controller 161 controls the horizontal driver 159 according to a cleaning pattern of a cuvette placed at each cleaning position for each pivot cycle so as to locate the nozzle 115 for a cleaning liquid according to that cleaning position. More specifically, the controller 161 identifies a cuvette 72 placed at each cleaning position for each pivot cycle. After the cuvette 72 is identified, the controller 161 specifies a cleaning pattern set to the identified cuvette 72, and specifies a cleaning operation at the placed cleaning position from the specified cleaning pattern. Then, the controller 161 controls the horizontal driver 159 according to the specified cleaning operation to translate the plurality of nozzles 115 in the horizontal direction, thereby locating the nozzle 115 according to the specified cleaning operation at the cleaning position. For example, when the specified cleaning operation is ejection of a high- or low-concentration waste liquid or water cleaning, the controller 161 controls the horizontal driver 159 to locate the pure water nozzle 115a at that cleaning position. When the specified cleaning operation is alkaline cleaner cleaning, the controller 161 controls the horizontal driver 159 to locate the alkaline cleaner nozzle 115b at that cleaning position. When the specified cleaning operation is acidic cleaner cleaning, the controller 161 controls the horizontal driver 159 to locate the acidic cleaner nozzle 115c at that cleaning position. The nozzles 115 are translated by the horizontal driver 159 during, for example, a pivot period of the reaction disc 71 or an initial stage of a stop period of the reaction disc.

Upon completion of allocation of the nozzle 115 at each cleaning position, the controller 161 controls the vertical driver 155 to move the nozzle 115 located at that cleaning position downward. Then, a cleaning liquid according to the cuvette 72 at that cleaning position is discharged from the nozzle 115. After the cleaning liquid is discharged, the controller 161 controls the vertical driver 155 to move the nozzle 115 at the cleaning position upward. After the nozzle 115 is moved upward, the reaction disc 71 is pivoted through the pivot angle. Then, the allocation of the nozzles 115 at cleaning positions and discharging of cleaning liquids are similarly repeated.

In this manner, the nozzle 115 at each cleaning position discharges a cleaning liquid according to the cleaning pattern set to the cuvette 72 at that cleaning position under the control of the controller 161.

As described above, the automatic analyzer 1 according to the second example includes the nozzles (the pure water nozzle 115a, alkaline cleaner nozzle 115b, and acidic cleaner nozzle 115c) according to the types of cleaning liquids for each cleaning position. Also, the automatic analyzer 1 includes the horizontal support mechanism (arms 157) used to horizontally move these nozzles 115. The automatic analyzer 1 actuates the horizontal support mechanism to locate the nozzle 115 corresponding to the cuvette 72 to be cleaned at the cleaning position, so as to clean that cuvette 72 using the set cleaning pattern.

Therefore, the automatic analyzer 1 according to the second example can clean a cuvette using a cleaning pattern according to each individual measurement item. In this way, the automatic analyzer 1 according to the second example can improve the cleaning efficiency of cuvettes.

(Second Embodiment)

Optimal reaction times of mixed liquids are different depending on measurement items and reagents. Thus, a reaction time is often wanted to be extended to be longer than a normal reaction time. As an extension method of the reaction time, a method of setting a lower pivot speed of a reaction disc 71 is available. However, with this method, a processing speed (throughput) considerably drops. As another extension method, a method of skipping a cleaning operation for an extension target cuvette may be used. However, by simply skipping a cleaning operation, a cleaner or water used to clean neighboring cuvettes may be mixed into the extension target cuvette. An automatic analyzer according to the second embodiment can extend a reaction time of each individual cuvette while suppressing a throughput from dropping and also sample measurement results from being worsened. The automatic analyzer according to the second embodiment will be described below. In the following description, the same reference numerals denote components having substantially the same functions as those of the first embodiment, and a repetitive description will be allowed only when it is required.

Cleaning pattern setting processing by a setting unit 50 according to the second embodiment will be described first. FIG. 16 is a table showing examples of cleaning patterns set by the setting unit 50 according to the second embodiment. As shown in FIG. 16, a cleaning pattern according to the second embodiment includes at least one "no cleaning operation" (OFF) as a cleaning operation. In other words, the setting unit 50 can set ON/OFF of a cleaning operation for each cleaning position. For example, in pattern F, a cleaning operation is skipped (it is not executed) at position a. That is, pattern F can extend a reaction time by one revolving cycle. Also, in pattern G, cleaning operations are skipped at all cleaning positions. That is, pattern G can extend a reaction time by one analysis cycle. Note that when pattern G is set, a cuvette 72 is not cleaned in that analysis cycle. Therefore, a cleaning pattern of an analysis cycle next to that in which pattern G is set is required to be set so as to clean that cuvette 72. Note that a cleaning position of cleaning operation=OFF can be arbitrarily set via an operation unit 40.

The setting unit 50 sets a cleaning pattern of a target measurement item according to user's instructions via the operation unit 40. Then, the setting unit 50 sets the set cleaning pattern to a cuvette 72 used in measurement of the target measurement item. FIG. 17 is a table showing an example of a cleaning pattern set to the cuvette 72 by the setting unit 50. As shown in FIGS. 16 and 17, pattern F in FIG. 16 is set to cuvette G. In this manner, various cleaning patterns are set to respective cuvettes 72.

Figure 18:
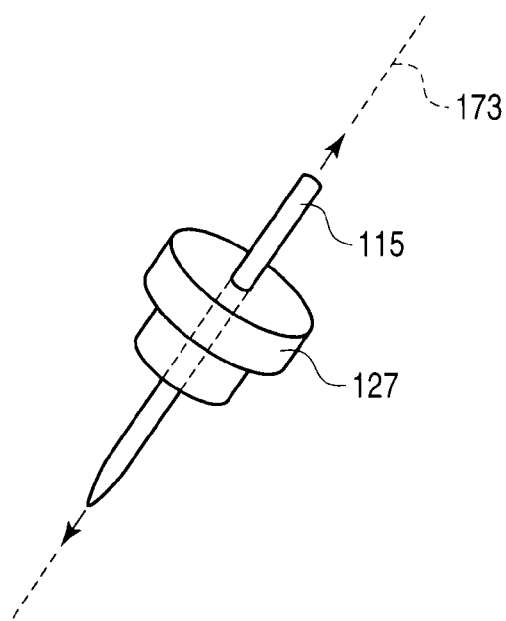
FIG. 18 is a perspective view for explaining the structure of a nozzle and cover according to the second embodiment.
Figure 19:
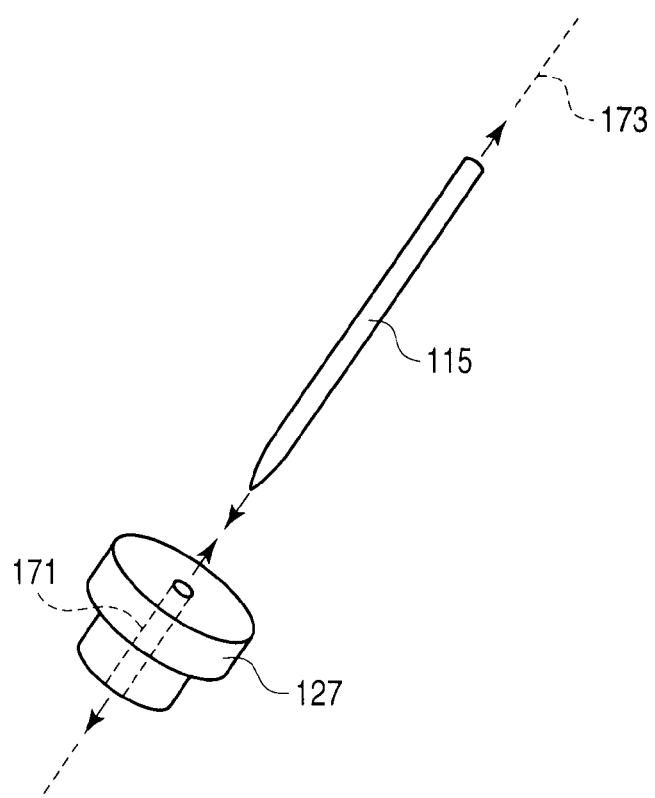
FIG. 19 is another perspective view for explaining the structure of a nozzle and cover according to the second embodiment.

A structure of a nozzle 115 and cover 127 required to extend a reaction time will be described below. FIGS. 18 and 19 are perspective views for explaining the structure of the nozzle 115 and cover 127. As shown in FIGS. 18 and 19, the cover 127 has a through hole 171. The diameter of the through hole 171 is designed to have a size that allows the nozzle 115 to pass through it. Typically, the diameter of the through hole 171 is designed to be substantially equal to that of the nozzle 115. The nozzle 115 and cover 127 are supported by a support mechanism (not shown) to be individually and vertically movable along an axial center 173, so that their axial centers 173 nearly match. The nozzle 115 and cover 127 are supported, so that the axial center 173 extends along the vertical direction.

FIG. 20 is a functional block diagram of a cleaning system of an automatic analyzer 1 according to the second embodiment. As shown in FIG. 20, the automatic analyzer 1 according to the second embodiment has a display unit 32, the operation unit 40, the setting unit 50, a cleaning mechanism controller 181, a valve driver 143, a first vertical driver 183, and a second vertical driver 185 to have a system controller 60 as a core. Note that the display unit 32, operation unit 40, setting unit 50, and valve driver 143 have already described previously, and a description thereof will not be repeated.

The controller 181 is a part of an analysis mechanism controller 12. The controller 181 controls the valve driver 143, first vertical driver 183, and second vertical driver 185 in accordance with a cleaning pattern set by the setting unit 50. The first vertical driver 183 is a part of an analysis mechanism driver 13. The first vertical driver 183 is driven under the control of the controller 181 to vertically move each nozzle 115 independently of the cover 127 in the vertical direction (axial center 173). The second vertical driver 185 is a part of the analysis mechanism driver 13. The second vertical driver 185 is driven under the control of the controller 181 to vertically move each cover 127 independently of the nozzle 115 in the vertical direction (axial center 173).

Operation examples of the nozzle 115 and cover 127 under the control of the controller 181 will be described below. FIGS. 21, 22, and 23 show the operation examples of the nozzle 115 and cover 127. FIG. 21 shows the positional relationship among the nozzle 115, cover 127, and cuvette 72 in a standby mode. FIG. 22 shows the positional relationship among the nozzle 115, cover 127, and cuvette 72 in a cleaning operation skip (OFF) mode. FIG. 23 shows the positional relationship among the nozzle 115, cover 127, and cuvette 72 in a cleaning operation mode.

As shown in FIG. 21, in the standby mode, the nozzle 115 and cover 127 are located at an initial position. The initial position is a location of both the nozzle 115 and cover 127 before downward movement. For example, at the initial position, the nozzle 115 is supported by a support mechanism (not shown) while being inserted in the through hole 171 of the cover 127.

The controller 181 specifies a cleaning operation of the cuvette 72 placed at a cleaning position. When it is specified to skip a cleaning operation (cleaning operation skip mode), the controller 181 controls the second vertical driver 185 to move the cover 127 downward in the vertical direction 173 to close an opening of the cuvette 72 by the cover 127, as shown in FIG. 22. In the cleaning operation skip mode, the nozzle 115 is not moved downward, and remains located at the initial position. In this manner, in the cleaning operation skip mode, the opening of the cuvette 72 whose reaction time is to be extended is closed by the cover 127. After an elapse of a predetermined time period (for example, at the end timing of the stop period of the reaction disc 71, in other words, at the end timing of a cleaning operation at another cleaning position), the controller 181 controls the second vertical driver 185 to move the cover 127 upward in the vertical direction 173, so as to locate the cover 127 at the initial position. Therefore, a possibility of entering a liquid such as a cleaning liquid into the extension target cuvette 72 can be reduced.

On the other hand, when it is specified to execute a cleaning operation (cleaning operation mode), the controller 181 controls the first and second vertical drivers 183 and 185 to move the nozzle 115 and cover 127 downward in the vertical direction 173, as shown in FIG. 23. More specifically, the cover 127 is moved downward until it closes the opening of the cuvette 72 as in the cleaning operation skip mode. The nozzle 115 is moved downward until it enters into the cuvette 72. The nozzle 115 and cover 127 may be moved downward at the same timing or different timings. After an elapse of a predetermined time period (for example, at the end timing of the stop period of the reaction disc 71, in other words, at the end timing of a cleaning operation), the controller 181 controls the first and second vertical drivers 183 and 185 to move the nozzle 115 and cover 127 upward in the vertical direction 173, thereby locating the nozzle 115 and cover 127 at the initial position.

With the above arrangement, the automatic analyzer 1 according to the second embodiment has the vertically movable cover 127. The automatic analyzer 1 closes the opening of the extension target cuvette 72 by the cover 127. As a result, a possibility of entering a liquid such as a cleaning liquid into the extension target cuvette 72 can be remarkably reduced. Also, the automatic analyzer 1 can individually set cleaning operations for respective cleaning positions by an independent driving mechanism. Therefore, the automatic analyzer 1 can extend a reaction time of only the extension target cuvette 72 without extending the reaction times of all the cuvettes placed at the plurality of cleaning positions. The pivot speed of the reaction disc 71 need not be lowered to extend a reaction time unlike in the conventional method, and the reaction time can be extended while maintaining the pivot speed. Therefore, the automatic analyzer 1 can extend a reaction time of each individual cuvette 72 while suppressing the throughput from dropping due to extension of the reaction time. In this manner, the automatic analyzer 1 according to the second embodiment can improve the cleaning efficiency of the cuvettes 72.

Note that a cleaning mechanism 89 in the second embodiment is configured to switching cleaning liquids by a channel switching valve 113. However, the second embodiment is not limited to this. For example, the cleaning mechanism 89 according to the second embodiment may be configured to switching cleaning liquids by a horizontal support mechanism (arms 157), as shown in FIGS. 13 and 14.

The first and second embodiments can be combined as needed. That is, during one pivot cycle, a cleaning operation may be executed at a certain cleaning position, and a cleaning operation may be skipped at another cleaning position.

(First Modification)

In the first and second embodiments, the cover 127 completely closes the opening of the cuvette 72. More specifically, as shown in, for example, FIGS. 22 and 23, the cover 127 has a distal end portion which can fit into the opening of the cuvette 72. When this distal end fits into the opening, the cuvette 72 is hermetically closed. The plurality of cuvettes 72 are alternately closed by the cover 127. When the opening of one cuvette 72 is contaminated, another cuvette 72 may be contaminated via the distal end portion of the cover 127. A cover according to the first modification will be described below. In the following description, the same reference numerals denote components having substantially the same functions as those in the first and second embodiments, and a repetitive description will be allowed only when it is required.

Figure 24:
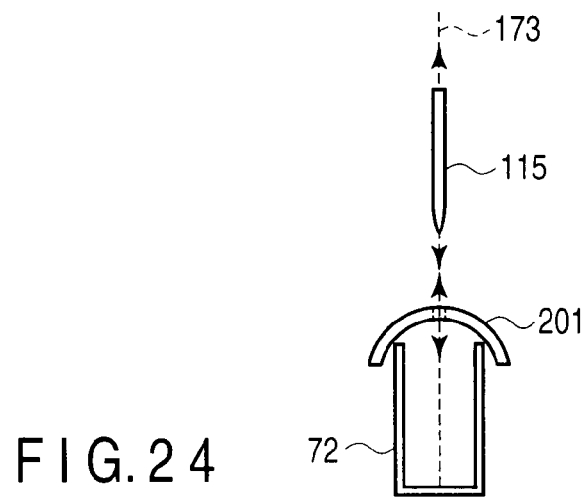
FIG. 24 is a sectional view showing the structure of a cover according to a first modification.

FIG. 24 is a sectional view showing the structure of a cover 201 according to the first modification. As shown in FIG. 24, the cover 201 according to the first modification has a shape that can cover an opening without fitting into the cuvette 72. For example, the cover 201 has an umbrella shape. The cover 201 has a through hole for the nozzle 115. The cover 201 and nozzle 115 are supported by a support mechanism (not shown) to be individually and vertically movable along the axial center 173, so that their axial centers 173 nearly match.

Figure 25:
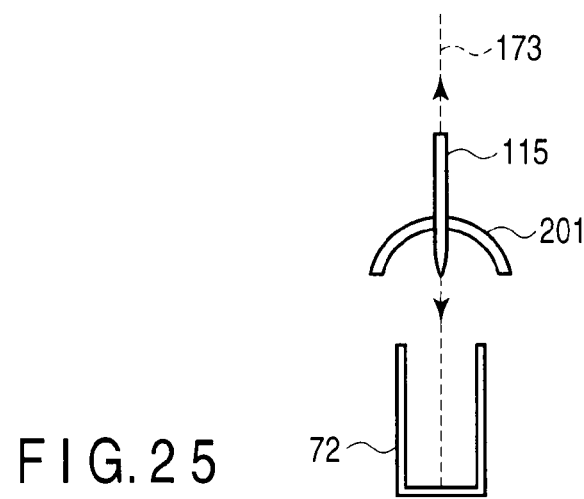
FIG. 25 is a sectional view showing the structure of the cover fixed to a nozzle in FIG. 24.

Note that the cover 201 may be fixed to a position of the nozzle 115 where it can cover the opening of the cuvette 72 when the nozzle 115 is moved downward, as shown in FIG. 25. Unlike in the above structure, the cover 201 does not have a portion which can fit into the opening of the cuvette 72.

Therefore, the cover 201 hardly contaminates the cuvette 72 compared to the cover 127 according to the first and second embodiments.

(Second Modification)

The cover according to the first and second embodiments has a through hole that allows the nozzle to pass through it. A cover according to the second modification has a slit that allows the nozzle to pass through it. The cover according to the second modification will be described below. In the following description, the same reference numerals denote components having substantially the same functions as those in the first and second embodiments, and a repetitive description will be allowed only when it is required.

Figure 26:
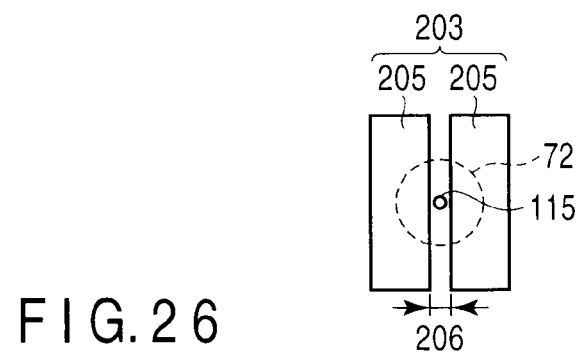
FIG. 26 is a plan view showing the structure of a cover according to a second modification.

FIG. 26 is a plan view showing the structure of a cover 203 according to the second modification. Assume that the nozzle 115 is moved from the front side to the back side or vice versa on the plane of the drawing in FIG. 26. The cover 203 is configured by a plurality of cover portions 205, as shown in FIG. 26. For example, the cover 203 is configured by two cover portions 205. The plurality of cover portions 205 have a slit 206 having a size that allows the nozzle 115 to pass through between the plurality of cover portions 205. The number of cover portions 205 may be three or more.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An automatic analyzer comprising:
a reaction disc configured to hold plural cuvettes including a particular cuvette which contains a sample and a reagent;
a cleaning mechanism configured to clean the particular cuvette using a nozzle with washing water;
a cover configured to be movable along an axis of the nozzle independent of the nozzle and to cover an opening of the particular cuvette;
a photometry mechanism configured to irradiate the particular cuvette pivoted by the reaction disc with light, and to convert light transmitted through a sample and a reagent into an absorbency to generate measurement data;
and
a controller configured to:
determine whether a reaction time for individual ones of said plural cuvettes is to be extended and to independently control the nozzle and cover of respective of said plural cuvettes, in accordance with whether it is determined that the reaction time of a particular cuvettes is to be extended or not, and
move, when it is determined that the reaction time set to the particular cuvette is to be extended, the cover downward along the axis of the nozzle so as to make the cover close the opening of the particular cuvette, and also inhibit part of the nozzle including a distal end of the nozzle from entering the particular cuvette, and
move, when it is determined that the reaction time set to the particular cuvette is not to be extended, the cover and nozzle downward along the axis to make the cover close the opening and to cause the part of the nozzle to enter the particular cuvette and clean the particular cuvette with washing water.

2. The automatic analyzer according to claim 1, wherein:
when it is determined that the reaction time set to the cuvette is to be extended, the controller is configured not to move the cover and the nozzle downward while the plurality of cuvettes are rotating by the response disc and to move the cover downward while the plurality of the cuvettes are stopped by the response disc, and
when it is determined that the reaction time set to the cuvette is not to be extended, the controller is configured not to move the cover and the nozzle downward while the plurality of cuvettes are rotating by the response disc and to move the cover and the nozzle downward while the plurality of cuvettes are stopped by the response disc.

\* \* \* \* \*